United States Patent [19]

Wilson et al.

[11] 4,042,601

[45] Aug. 16, 1977

[54] SIX MEMBERED HETEROCYCLIC OXATHIO COMPOUNDS

[75] Inventors: Richard A. Wilson, Westfield; John V. Pascale, Jackson; Manfred Hugo Vock, Locust, all of N.J.

[73] Assignee: International Flavors & Fragrances Inc., New York, N.Y.

[21] Appl. No.: 676,390

[22] Filed: Apr. 12, 1976

Related U.S. Application Data

[63] Continuation-in-part of Ser. No. 594,310, July 8, 1975.

[51] Int. Cl.$^2$ ............................................. C07D 327/06
[52] U.S. Cl. ................................................. 260/327 M
[58] Field of Search .......................... 260/327 M, 346.7

[56] References Cited

U.S. PATENT DOCUMENTS 3,025,214  3/1962  Eden ........................................ 167/33

OTHER PUBLICATIONS

Kipnis, et al., J.A.C.S. 71:3555 (1949).
Djerassi, et al., J.A.C.S. 75:3704–3708 (1953) (cited as Chem. Abs. 48:11476–11478).
Stevenson, et al., J.A.C.S. 96:1067–1071 (1974).
Marshall, et al., J. Chem. Soc. 1959, pp. 2360–2363 (cited as Chem. Abs. 54:2341–2342).
Eliel, et al., J. Org. Chem. 35, No. 8, pp. 2716–2722 (1970).
Pihlaja, et al., Acta Chem. Scand., 1970, 24(b), 2257–2258, (Chem. Abs. 74:3566c).

*Primary Examiner*—Cecilia M. S. Jaisle
*Attorney, Agent, or Firm*—Arthur L. Liberman; Harold Haidt; Franklin D. Wolffe

[57] ABSTRACT

One or more five or six membered oxathio heterocyclic compounds having one sulfur atom and one oxygen atom, such as an oxathiolane or an oxathiane, is used to alter, modify or enhance the flavor or aroma of a foodstuff, chewing gum or medicinal product. Among said oxathio heterocyclic compounds are the seven novel compounds:
2,6-dimethyl-2-phenyl-1,3-oxathiane
2-isobutyl-6-methyl-1,3-oxathiane
ethyl-2,6-dimethyl-1,3-oxathiane-2-acetate
2,6-dimethyl-2-acetyl-1,3-oxathiane
2-n-nonyl-6-methyl-1,3-oxathiane
2-isobutyl-1,3-oxathiolane
7-methyl(6-oxa-10-thiaspiro) 4.5-decane

2 Claims, 14 Drawing Figures

NMR SPECTRUM for the compound produced according to EXAMPLE VI

1000 Hz SWEEP WIDTH

NMR SPECTRUM for the compound produced according to EXAMPLE IX

I.R. SPECTRUM for the compound produced according to EXAMPLE IX

NMR SPECTRUM for the compound produced according to EXAMPLE XI

I.R. SPECTRUM for the compound produced according to EXAMPLE XI

NMR SPECTRUM for the compound produced according to EXAMPLE XII

I.R. SPECTRUM for the compound produced according to EXAMPLE XII 4,042,601

SIX MEMBERED HETEROCYCLIC OXATHIO COMPOUNDS

This Application is a continuation-in-part of U.S. application for Letters Pat. Ser. No. 594,310, filed on July 8, 1975 co-pending.

BACKGROUND OF THE INVENTION

The present invention concerns the altering, modification or enhancement of the flavor or aroma of a foodstuff, chewing gum, or medicinal product. More particularly, this invention relates to the use of a five membered or six membered heterocyclic compound containing one oxygen atom and one sulfur atom such as an oxathiolane or an oxathiane, to alter, modify or enhance the flavor and/or aroma characteristics of a foodstuff, chewing gum or medicinal product.

The terms "alter" and "modify" in their various forms are used herein to mean the supplying or imparting of a flavor or aroma characteristic or note to an edible substance, or augmenting an existing flavor or aroma characteristic where the natural flavor or intrinsic odor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note.

The term "foodstuff" as used herein includes both solid and liquid ingestible materials, which usually do, but need not, have nutritional value. Thus, foodstuffs include meats, gravies, soups, convenience foods, beverages, dairy products, candies, vegetables, cereals, soft drinks, and the like.

The term "chewing gum" is intended to mean a composition which comprises a substantially water-insoluble, chewable plastic gum base such as chicle, or substitutes therefor, including jelutung, guttakay rubber and/or certain comestible natural or synthetic resins or waxes. Incorporated within the gum base, in admixture therewith may be plasticizers or softening agents, e.g. glycerine; and a flavoring composition which incorporates the heterocyclic oxathio compound of our invention, and, in addition, sweetening agents which may be sugars, including sucrose or dextrose and/or artificial sweeteners including dipeptides, cyclamates and saccharin. Other optional ingredients may also be present.

The term "medicinal product" includes both solids and liquids which are ingestible, non toxic materials having medicinal value such as cough syrups, cough drops, toothpaste, aspirin and chewable medicinal tablets.

PRIOR ART

Various heterocyclic compounds containing three, four, or five sulfur atoms in the ring have been said to be flavorful or aroma-imparting. Thus, Chang et al in *Chemistry and Industry* for Nov. 23, 1968, pages 1639–1641, identified 3,5-dimethyl-1,2,4-trithiolane in the volatile flavor compounds of boiled beef; and Wada et al in U.S. Pat. No. 3,503,758 issued on Mar. 31, 1970, describes pentathiepane and various tetrathiepanes as having a good aroma and, therefore, useful as flavor enhancers. The tetra- and pentathiepanes possess a sweet, meaty flavor. Polyalkyl symmetrical trithianes have been disclosed in copending U.S. application Ser. No. 166,683 filed July 28, 1971, as having a sweet, nutty aroma and taste and suitable for fruit, nut and meat flavors.

Five or six membered heterocyclic compounds having two sulfur atoms in the ring are disclosed to be useful in altering the flavor or aroma of foodstuffs in U.S. application Ser. No. 272,396 filed on July 17, 1972. Such dithio heterocyclic compounds in that case include dithiolanes and dithianes, which may be alkyl substituted or non-alkyl substituted. According to U.S. application Ser. No. 272,396, dithio heterocyclic compounds found suitable are represented by one of the following formulae:

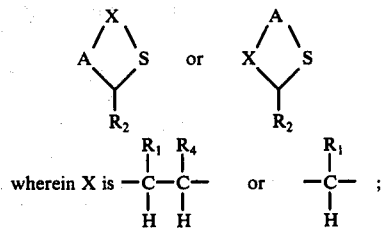

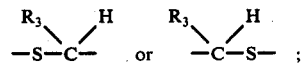

and A is either

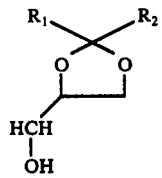

and each of $R_1$ to $R_4$ is hydrogen or a lower alkyl radical of 1 to 3 carbon atoms.

Although a number of meta-dioxanes and meta-dioxolanes are indicated in the prior art to have specific organoleptic properties, such properties of the meta-dioxanes and meta-dioxolanes are different in kind from the aromas and tastes of the heterocyclic oxathio compounds of our invention. Thus, German Offenlegungschrift No. 2,233,245 discloses 1,3 dioxolanes of the formula:

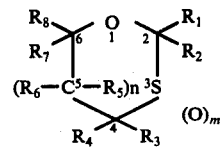

wherein $R_1$ or $R_2$ can be, interalia, ethyl or propyl as baked goods aromas.

Firmenich Published Dutch application Ser. No. 7,509,027, published on Feb. 4, 1976 and based upon two Swiss Priority Documents:
i. 10619/74, filed Aug. 2, 1974; and
ii. 520/75, filed Jan. 16, 1975,
discloses for use as flavorants various oxathiolane derivatives. Claim 1 reads as follows:

"1. Process for the preparation of flavored and/or perfumed products, characterized by the incorporation of a compound of structure 1:

$$\begin{array}{c} R_8 \diagdown \phantom{xx} O \phantom{xx} \diagup R_1 \\ \phantom{xx} \diagup 6 \phantom{x} 1 \phantom{x} 2 \diagdown \\ R_7 \phantom{xxxxxxxxxx} R_2 \\ (R_6{-}C^5{-}R_5)n \phantom{x} {}^3S \\ \phantom{xxxxxxxx} \diagdown \phantom{xxx} (O)_m \\ \phantom{xxxxxx} R_4 \phantom{xx} R_3 \end{array}$$

in which:
a. $m = n = 0$ or 1, while each of $R^1$ to $R^8$ represents H or a saturated or unsaturated, linear or ramified alkyl with 1–11 C's or;
b. $n = 1$ and $m = 0$ or 1, while each of $R^1$, $R^2$, $R^3$ and $R^4$ have the above-mentioned meaning, $R^5 = R^7 = $ H, $R^6 = R^8$ the carbons at positions 5 and 6 to which they are bound, from a substituted or unsubstituted cyclopentane or cyclohexane ring, or
c. $n = 1$ and $m = 0$ or 1, while $R^1 = R^3 = R^5 = R^6 = R^7 = $ H, $R^2$ is H or lower alkyl, $R^4$ is para substituted or unsubstituted phenyl or substituted or unsubstituted cyclohexenyl and $R^8$ is lower alkyl or
d. $n = 1$ and $m = 0$ or 1 while $R^1 = R^3 = R^5 = R^6 = R^7 = $ H, $R^2$ is para substituted or unsubstituted phenyl or substituted or unsubstituted cyclohexenyl, $R^4 = $ lower alkyl or H, $R^8$ is lower alkyl or H, as well as an animal feed, a beverage, a pharmaceutical preparation, a tobacco product, a different odorant or a perfume base."

The Firmenich Published Dutch Application has a publication date of Feb. 4, 1976 which is subsequent to the filing date of the parent case, Ser. No. 594,310, which is July 8, 1975.

Kipnis et al. J. Am. Chem. Soc. 71, 3555 (1949) discloses that 2-isopropyl-1,3-oxathiolane and 2-phenyl-1,3-oxathiolane have pleasant aromas. However, this disclosure does not seem to indicate the usefulness in this invention for augmenting, modifying or enhancing the flavor or aroma of a foodstuff, chewing gum or medicinal products.

Beilstein discloses the following:

| Compound Structure | Reference | Organoleptic Property |
|---|---|---|
|  | E II 19:10 | Camphor-like smelling liquid |
|  | E II 19:10 | Liquid of camphor-type odor |
|  | E II 19:12 | Ether-like smelling oil |
|  | E II 19:12 | Liquid of camphor-like smell |
|  | E II 19:12 | Camphor-type smelling liquid |
|  | E II 19:12 | Liquid of pleasant camphor-like aroma |
|  | E II 19:12 | Camphor-like smelling liquid |
| 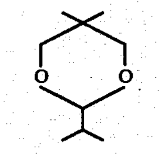 | E II 19:13 | Liquid of intense camphor-like odor |
|  | E II 19:14 | Liquid with camphor-like odor |
|  | E II 19:14 | Liquid with camphor-like odor (impure) |
|  | E II 19:14 | Liquid with intense odor, reminiscent of heptanal |
| 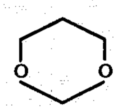 | E I 19:609 | Acetal-like smelling liquid |

Chem. Abstracts 69; 96605 Z discloses the following organoleptic properties for various metadioxanes:

| Compound Structure | Organoleptic Property |
|---|---|
| 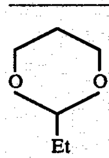 | Strong, vegetables |
| 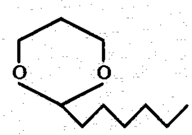 | Strong, grassy, jasmine |

-continued

| Compound Structure | Organoleptic Property |
|---|---|
| (Me, Et substituted dioxane) | Strong, vegetable |
| (dioxane with alkyl chain) | Strong, grassy, jasmine |
| (dioxane with alkyl chain) | Strong, jasmine |
| (Et, alkyl substituted dioxane) | Strong, jasmine |
| (dioxane with alkyl chain) | Medium, jasmine |
| (Et substituted dioxane) | Strong, sharp, vegetables |
| (dimethyl dioxane) | Strong, jasmine |
| (Et substituted dioxane) | Strong, musty, slightly chilly |
| (substituted dioxane) | Medium, musty, slightly chilly |
| (substituted dioxane) | Medium, musty, mushroom |

-continued

| Compound Structure | Organoleptic Property |
|---|---|
| (Et substituted dioxane) | Medium, vegetables, flower note |
| (Et substituted dioxane) | Weak; gardenia scent |

SUMMARY OF THE INVENTION

In accordance with this invention it has been found that certain five or six membered heterocyclic compounds having one sulfur atom and one oxygen atom in the ring (hereinafter called "oxathio heterocyclic compounds"), a number of which are novel compounds, are useful in altering, modifying or enhancing the flavor or aroma of a foodstuff, chewing gum or medicinal product. Such oxathio heterocyclic compounds include oxathiolanes and oxathianes, which may be alkyl substituted, carboxyalkyl substituted and/or acyl substituted. The oxygen atom and the sulfur atom in the ring are separated by one carbon atom. Thus, the oxathio heterocyclic compounds found suitable according to this invention may be represented by the following formula:

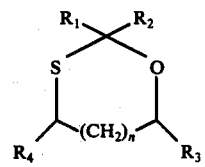

wherein $n$ is 0 or 1; $R_1$ is hydrogen or $C_1-C_9$ alkyl; $R_2$ is hydrogen, lower alkyl, aryl, carboalkoxy or alkanoyl; or $R_1$ and $R_2$ taken together complete a carbocyclic ring having from five up to nine carbon atoms; $R_3$ and $R_4$ are the same or different and are each hydrogen or lower alkyl; with the sum of the carbon atoms in $R_1$, $R_2$, $R_3$ and $R_4$ being greater than or equal to 1; and the sum of the carbon atoms in $R_1$ and $R_2$ being less than or equal to nine.

Within the aforementioned genus of compounds are seven novel compounds which have unexpected, unobvious and advantageous organoleptic properties with respect to their individual abilities to be used to modify or enhance or alter the taste and/or aroma of foodstuffs and/or chewing gum and/or medicinal products. These seven novel compounds as well as their structures are set forth in the following table:

| Novel Oxathio Heterocyclic Compound | Structure |
|---|---|
| 7-methyl (6-oxa-10-thiaspiro) 4.5-decane | 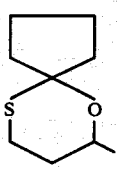 |
| 2,6-dimethyl-2-phenyl-1,3-oxathiane | 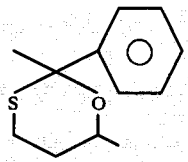 |
| 2-isobutyl-6-methyl-1,3-oxathiane | 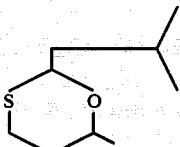 |
| Ethyl-2,6-dimethyl-1,3-oxathiane-2-acetate | 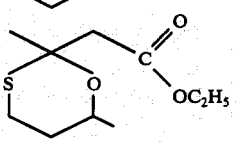 |
| 2,6-dimethyl-2-acetyl-1,3-oxathiane | 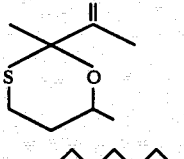 |
| 2-n-nonyl-6-methyl-1,3-oxathiane | 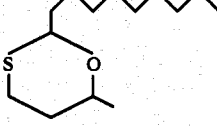 |
| 2-isobutyl-1,3-oxathiolane | 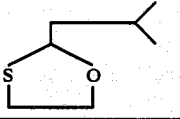 |

DESCRIPTION OF THE PREFERRED EMBODIMENTS

Although the seven oxathio heterocyclic compounds of this invention are novel, many of the oxathio heterocyclic compounds of parent application Ser. No. 594,310, filed on July 8, 1975 are old compounds, but have not heretofore been recognized as being useful flavoring or aromatising agents for foodstuffs, chewing gums or medicinal products. The aforementioned oxathio heterocyclic compounds of this invention in many instances have notes which may be described as:

Sulfury/Roasted;
Roasted;
Spearmint-like;
Roasted almond-like;
Heavy roasted;
Coffee-like;
Sweet/sulfury/meaty;
Gasey;
Fruity;
Albedo-like;
Citrus;
Yeasty;
Vegetable;
Sweet;
Floral;
Beefy;
Green, green vegetable (e.g. cucumber);
Leek;
Garlic;
Celery;
Tomato;
Horseradish;
Watercress;
Berry;
Butternut;
Rum;
Grapefruit;
Black Pepper;
Spicy;
Cantelope;
Fig;
Parsley;
Tropical Fruit; and
Quince,
which make them especially suitable for the following flavors:
Meat;
Cooked Fruit;
Apple;
Citrus Fruit;
Tropical Fruit;
Black Currant;
Vegetable;
Tomato;
Leek;
Horseradish;
Garlic;
Rum;
Butterscotch;
Spice; and
Black Pepper.

The oxathio heterocyclic compounds of our invention may be produced according to a process which comprises the step of reacting a carbonyl compound (e.g. an aldehyde or a ketone) with an $\alpha$ or $\beta$ hydroxy alkane thiol in the presence of a catalyst such as paratoluene sulfonic acid according to the following reaction:

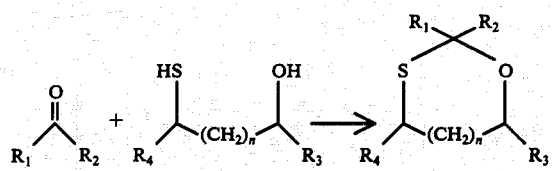

wherein $n$ is zero or 1; $R_1$ is hydrogen or $C_1$–$C_9$ alkyl; $R_2$ is hydrogen, lower alkyl, aryl, carboalkoxy or alkanoyl; or $R_1$ and $R_2$ taken together form a carbocyclic ring containing from 5 up to 9 carbon atoms; $R_3$ and $R_4$ are the same or different, and are each hydrogen or lower alkyl; the sum of the number of carbon atoms in $R_1$ and $R_2$ being less than or equal to 9; and the sum of the number of carbon atoms in $R_1$, $R_2$, $R_3$ and $R_4$ not being less than 1.

The following table sets forth examples of specific reactants and the resulting products produced using the process set forth above:

TABLE I

| CARBONYL COMPOUND | α Or β-HYDROXY ALKANETHIOL REACTANT | HETEROCYCLIC OXATHIO COMPOUND | STRUCTURE |
|---|---|---|---|
| acetaldehyde | 2-mercapto ethanol | 2-methyl-1,3-oxathiolane | |
| acetaldehyde | 4-mercapto-2-butanol | 2,6-dimethyl-1,3-oxathiane | |
| benzaldehyde | 4-mercapto-2-butanol | 6-methyl-2-phenyl-1,3-oxathiane | 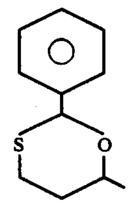 |
| diacetyl | 4-mercapto-2-butanol | 2-acetyl-2,6-dimethyl-1,3-oxathiane | 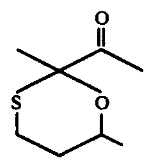 |
| acetone | 4-mercapto-2-butanol | 2,2,6-trimethyl-1,3-oxathiane | |
| isovaleraldehyde | 4-mercapto-2-butanol | 2-isobutyl-6-methyl-1,3-oxathiane | |
| acetone | 2-mercapto ethanol | 2,2-dimethyl-1,3-oxathiolane | |
| isovaleraldehyde | 2-mercapto ethanol | 2-isobutyl-1,3-oxathiolane | |
| acetophenone | 4-mercapto-2-butanol | 2,6-dimethyl-2-phenyl-1,3-oxathiane | 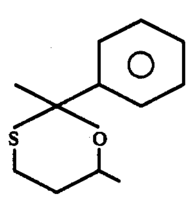 |
| ethyl acetoacetate | 4-mercapto-2-butanol | ethyl-2,6-dimethyl-1,3-oxathiane-2-acetate | 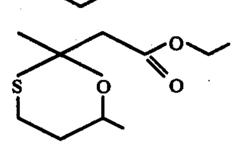 |

TABLE I-continued

| CARBONYL COMPOUND | α Or β-HYDROXY ALKANETHIOL REACTANT | HETEROCYCLIC OXATHIO COMPOUND | STRUCTURE |
|---|---|---|---|
| n-decanal | 4-mercapto-2-butanol | 6-methyl-2-nonyl-1,3-oxathiane | 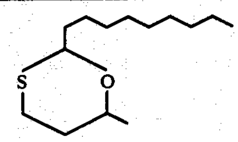 |
| cyclopentanone | 4-mercapto-2-butanol | 7-methyl(6-oxa-10-thiaspiro)4.5-decane | 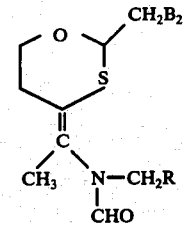 |

Methods for preparing the compounds of our invention are set forth in a number of literature references, examples of which are set forth as follows:

A. Preparation of Oxathiolanes

Keskinen, et al, Tetrahedron, Vol. 28, pages 3943-3955, "Properties and Reactions of 1,3-Oxathiolanes" (Discusses preparation and conformational properties of 2-alkyl-5-methyl-1,3-oxthiolanes and 2,2-dialkyl-5-methyl-1,3-oxathiolanes);

Chem Abstracts, Vol. 44:1096c, F. Kepnis and J. Ornfelt, J. Am. Chem. Soc. 71, 3555 (1949) (Reaction of mercapto-ethanol and isobutyraldehyde);

Chem Abstracts, Vol 5395d, U.S. Pat. No. 2,500,155, issued March 14, 1950, Rohm & Haas Col, (Preparation of ethyl-1,3-oxathiolane-2-acetate);

Chem Abstracts, Vol 45:4746e, British Pat. No. 642,253, August 30, 1950, General Aniline & Film Corp, (Rection of vinyl ethers with thios);

Chem Abstracts, Vol 47:6399f, E. D. Bergmann et al, Rec. Trav. Chim. 71:200-12(1950) (Preparation of 2-methyl-2-isobutyl-1,3-oxathiolane);

Chem Abstracts 48:11476i, C. Djerassi and M. Gorman, J. Am. Chem. Soc. 75:3704-8(1953)(Preparation of 1,3-oxathiolanes);

Chem Abstracts, Vol 49:1704c, A. R. Pinder and H. Smith, J. Chem. Soc. 113-20 (1956)(Preparation of 2-methyl-2-phenyl-1,3-oxathiolane);

Chem Abstracts, Vol. 49:6294c, L. F. Fieser, J. Am. Chem. Soc. 76:1945-7(1954)(Preparation of ethylene thioketals)

Chem. Abstracts, Vol 50:956e, C. Djerassi et al, J. Am. Chem. Soc. 77:568-71(1955)(Preparation of 2-methyl-2-ethyl-5-phenyl-1,3-oxathiolane)

Chem Abstracts, Vol. 53:5240h, E. Djerassi et al, J. Am. Chem. Soc. 80:4723-32(1958)(Synthesis of 1,3-oxathiolanes)

Chem Abstracts, Vol. 2341g, J. R. Marshall and H. A. Stevenson, J. Chem. Soc. 2360-3(1959) (Preparation by reaction of aldehydes or ketones with monothioglycols)

Chem Abstracts, Vol 45:13138i, K. K. Georgieff and A. Dupre; Can. J. Chem. 37:1104-8(1959) (Preparation of 2-methyl-1,3-oxathiolane)

Chem Abstracts, Vol 54:21102a, H. E. Simmons Jr. and D. W. Wiley, J. Am. Chem. Soc. 82:2288-96(1960) (Preparation of 2,2-bis-(chlorodifluoromethyl)-1,3-oxathiolane)

B. Preparation of Oxathianes

Chem Abstracts, Vol 48:11476h, C. Djerassi and M. Gorman, J. Am. Chem. Soc. 75:3704-8(1953) (Preparation of 1,3-oxathianes)

Chem Abstracts, Vol. 53:5240h, C. Djerassi et al, J. Am. Chem. Soc. 80:4723-4732(1958) (Preparation of 1,3-oxathianes)

Chem Abstracts, Vol. 54:2341g, J. R. Marshall and H. A. Stevenson, J. Chem. Soc. 2360-3(1959) (Preparation of 1,3-oxathianes by interaction of aldehydes and ketones with monothioglycol)

Chem Abstracts, Vol. 55:25949d, C. S. Rondestvedt Jr., J. Org. Chem. 26:2247-53(1961)(Preparation of 2-isopropyl-5,5-diethyl-1,3-oxathiane and 2-phenyl-5,5-diethyl-1,3-oxathiane)

Chem Abstracts, Vol. 69:10405z, G. Pagani et al, Gazz. Chim. Ital. 97(12):1770-1803(1967)(Preparation of compounds of the general formula:

Chem Abstracts, Vol 74:3566c, K. Pihleja and P. Pasanen, Acta. Chem. Scand. 24(6):2257-8(1970); (Reaction of aldehydes or ketones with mercaptopropanols to give 18 alkyl substituted 1,3-oxathianes)

Chem Abstracts, Vol 75:19380u, U. Allington et al, Org. Magn. Resonause 3(1):37-43(1971)(Preparation and NMR spectra of 4-phenyl and 6-methyl-1,3-oxathianes and their α-substituted derivatives)

Chem Abstracts, Vol 75:140772b, P. Pasanen and P. Pihlaja, Acta. Chem. Scand. 25(5):1908-10(1971) (Novel route to alkylated 1,3-oxathianes)

Chem Abstracts, Vol 77:48146u, J. E. McCormick and R. S. McElhinney, Chem. Soc. Perkin Traus, 1(11):1335-42 (1972) (Preparation of 2-acetoxy-6-(phenylthio)-1,4-oxathiane).

The oxathio heterocyclic compounds of those invention, as well as those of parent application Ser. No. 594,310, filed on July 8, 1975, which can be produced as stated above, have useful organoleptic properties giving rise to their use as foodstuff or chewing gum or medicinal product flavor, or flavor adjuvants or flavor enhancers as set forth in an illustrative manner in the following table:

TABLE II

| HETEROCYCLIC OXIATHIO COMPOUND | STRUCTURE | FLAVOR PROPERTIES |
|---|---|---|
| 2-methyl-1,3-oxathiolane | 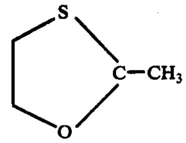 | Sulfury, metallic tomato aroma with a beet-like nuance and a sulfury, garlic, 58 metallic flavor with a celery-like nuance. |
| 2,6-dimethyl-1,3-oxathiane | 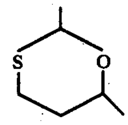 | Sweet, fruity, green aroma with an ethyl propionate-like nuance and a sweet fruity, berry flavor with green, vegetable, butternut-like, ethyl propionate-like, rum and grapefruit-like nuances. |
| 6-methyl-2-phenyl-1,3-oxathiane | 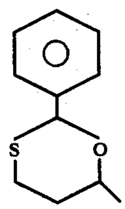 | At 2 ppm, roasted sulfury, "burnt-matches-like" aroma with roasted meat like roasted sulfury taste; at 5 ppm roasted notes, burnt notes as in heavy roasted almonds and coffee notes; at 10 ppm, green notes added. |
| 2-acetyl-2,6-dimethyl-1,3-oxathiane | 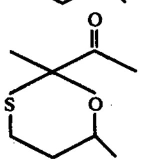 | At 0.1 ppm, a meaty/sulfury aroma and taste with a metallic note; at 0.2 ppm a sweet/meaty/sulfury aroma and taste with a burning sensation. |
| 2,2,6-trimethyl-1,3-oxathiane | 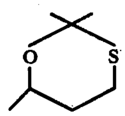 | Black-pepper-like, green, spicy aroma with a vegetable-like nuance and a black-pepper-like, spicy, green vegetable-like flavor with cucumber, burning and parsley nuances. |
| 2-isobutyl-6-methyl-1,3-oxathiane | 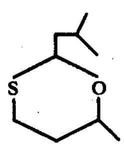 | Spicy, vegetable-like, cantelope aroma with green, fig and rum nuances, and a spice, vegetable, cantelope-like flavor with parsley, "tropical fruit"-like, quince, and burning nuances. |
| 2,2-dimethyl-1,3-oxathiolane | 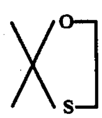 | Sulfury, garlic and tomato aroma with a sulfury, garlic and metallic flavor with a strong tomato nuance. |
| 2-isobutyl-1,3-oxathiolane | 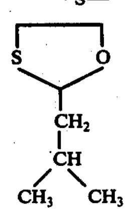 | Horseradish aroma and a horseradish, watercress, leek flavor with a burning nuance. |
| 2,6-dimethyl-2-phenyl,1-3-oxathiane | 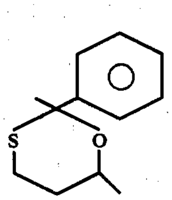 | Fruity, sulfury, vegetable aroma with yeasty and vitamin B complex-like nuances, and a fruity, sulfury, albedo-like flavor with yeasty and citrus-like nuances. |

TABLE II-continued

| HETEROCYCLIC OXIATHIO COMPOUND | STRUCTURE | FLAVOR PROPERTIES |
|---|---|---|
| ethyl-2,6-dimethyl-1,3-oxathiane-2-acetate | 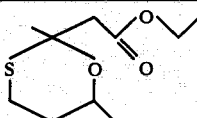 | At 10 ppm, sweet sulfury meaty aroma and taste. |
| 6-methyl-2-nonyl-1,3-oxathiane | 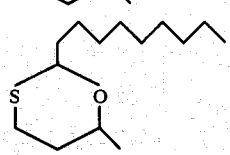 | At 0.01 ppm, a sweet sulfury roasted vegetable aroma and taste; at 0.02 ppm a sweet, sulfury roasted vegetable undertone; at 0.5 ppm, a definite spearment-like aroma; sweet, characteristic notes as found in spearmint. |
| 7-methyl(6-oxa-10-thiaspiro)4.5-decane | 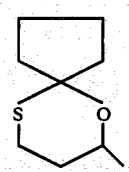 | Sweet, beefy, fruity aroma with a berry-like nuance and a sweet, fruity, floral flavor with berry, "mouthfeel" and green nuances. |

The compounds named and the structural formulae given herein contemplate and include cis-, trans- and other conformational isomers illustrated, for example, as follows:

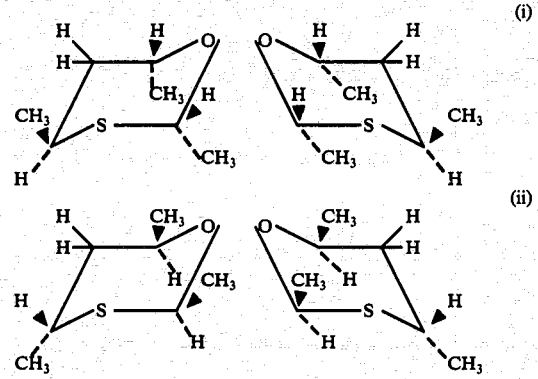

The oxathio heterocyclic compounds described herein may be employed either singly or in admixture comprising two or more thereof. Admixtures of two or more oxathio heterocyclic compounds offer the advantages of combining the beneficial and organoleptic qualities of each of the compounds into a total impact which may be superior or different from the characteristics of each of the sole ingredients. The formulator can simulate a wide variety of organoleptic characteristics to evoke a predetermined taste response on the part of the consumer.

Generally when used in conjunction with foodstuffs, chewing gum or medicinal products, the oxathio heterocyclic compound(s) is(are) admixed with one or more auxiliary flavoring adjuvants. The precise adjuvants employed will depend upon the ultimate use contemplated and the organoleptic character desired. Flavoring adjuvants are recognized in the art and are ingestibly acceptable or non-toxic. Such flavoring adjuvants include stabilizers, thickeners, surface active agents, conditioners, flavorants and flavor intensifiers.

Stabilizers include preservatives, e.g., sodium chloride; antioxidants, e.g. calcium and sodium ascorbate, ascorbic acid, butylated hydroxyanisole (mixture of 2- and 3-tertiary butyl-4-hydroxyanisole), butylated hydroxy toluene (2,6-ditertiary-butyl-4-methyl phenol), propyl gallate and the like, sequestrants, e.g., citric acid.

Thickeners include carriers, binders, protective colloids, suspending agents, emulsifiers and the like, e.g., agar-agar; carageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches; pectins and emulsifiers, e.g. mono- and diglycerides of fatty acids.

Surface active agents include emulsifying agents, e.g. fatty acids such as caproic acid, caprylic acid, palmitic acid, myristic acid and the like, mono- and di-glycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like; starch modifiers such as peracetic acid, sodium chlorite, sodium hypochlorite, propylene oxide, succinic anhydride and the like; buffers and neutralizing agents, e.g., sodium acetate, ammonium bicarbonate, ammonium phosphate, citric acid, lactic acid, vinegar and the like; colorants, e.g., carminic acid, cochineal, tumeric and curcumin and the like; firming agents such as aluminum sodium sulfate, calcium chloride and calcium gluconate; texturizers; anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferric pyrophosphate, ferrous gluconate and the like, riboflavin, vitamins, zinc sources such as zinc chloride, zinc sulfate and the like.

Flavorants and flavor intensifiers include organic acids, e.g., fatty saturated, unsaturated and amino acids; alcohols, e.g., primary and secondary alcohols; esters, carbonyl compounds including aldehydes and ketones, lactones; cyclic organic materials including benzene derivatives; alicyclics, heterocyclics such as furans, particularly 2-acetylfuran, pyridines, pyrazines and the like, sulfur-containing materials including thiazoles, thiols, sulfides, disulfides and the like; so-called flavor potentiators such as monosodium glutamate, guanylates, inosinates, natural and synthetic flavorants such as vanillin, natural gums and the like; spices, herbs, essential oils and extractives including anise, anise oil, alkanet root extract, bay leaves, capsicum extract and the like.

The specific flavoring adjuvant selected for use may be either solid or liquid, depending upon the desired physical form of the ultimate product, (i.e., foodstuff, chewing gum or medicinal product) whether simulated or natural, and should, in any event, be capable of providing an environment in which the oxathio heterocyclic compound can be dispersed or admixed to provide a homogeneous medium. In addition, selection of one or more flavoring adjuvants as well as the quantities thereof will depend upon the precise organoleptic character desired in the finished product; thus, in the case of flavoring compositions, ingredient selection will vary in accordance with the foodstuff to which the flavor and aroma are to be imparted. In contra-distinction, in the preparation of solid products, e.g., simulated foodstuffs, ingredients capable of providing normally solid compositions should be selected such as various cellulose derivatives.

Among the preferred flavoring adjuvants are: methyl thiazole alcohol, 2-methyl-1-butanethiol, 2-methyl-3-butanethiol, 4-mercapto-2-butanone, 3-mercapto-4-pentanone, 1-mercapto-2-propanone, benzaldehyde, furfural, furfuryl alcohol, 2-mercapto propionic acid, 2-methyl-2-pentenoic acid, alkyl pyrazine such as methyl pyrazine, 2-ethyl-3-methyl pyrazine and tetramethyl pyrazine, polysulfides such as dipropyl disulfide and methyl benzyl disulfide, alkyl thiophenes such as 2-butyl thiophene and 2,3-dimethyl thiophene, 5-methyl furfural, 2-acetyl furan, 2,4-decadienal, guiacol, phenyl acetaldehyde, δ-decalactone, d-limonene, acetoin, amyl acetate, maltol, ethyl butyrate, levulinic acid, piperonal, ethyl acetate, n-octanal, n-pentanal, hexanal and diacetyl. When used as a stewed vegetable flavoring it is especially preferred to combine the dithio heterocyclic compound with any one or more of a 2-alkyl thiazole such as 2-isobutyl thiazole, propyl propenyl disulfide, and propyl propenyl trisulfide.

Where used in conjunction with foodstuffs, chewing gum or medicinal products, the amount of oxathio heterocyclic compound employed in a particular instance can vary over a relatively wide range to achieve the desired organoleptic (taste and aroma) effects, and in accordance with ultimate consumer use. Thus, correspondingly greater amounts would be necessary in those instances where the ultimate foodstuff to be flavored or aromatized is relatively bland to the senses; whereas relatively lesser quantities may suffice for purposes of enhancing a composition merely deficient in a particular, desired flavor or aroma nuance or note. The primary requirement is that the amount selected be effective, i.e. sufficient to alter, modify or enhance the aroma and taste characteristics of the foodstuff to which it is added or incorporated.

Effective quantities of the oxathio heterocyclic compounds of our invention range from 0.03 ppm up to about 50 ppm based on the total weight of the foodstuff, chewing gum or medicinal product to which it or they are added depending upon whether a single oxathio heterocyclic compound is added or whether a mixture of oxathio heterocyclic compounds are added to the foodstuff, chewing gum or medicinal product. While larger concentrations can be used, they are less economical since additional amounts do not necessarily give equivalent incremental flavor enhancement, modification or alteration. In those instances where the oxathio heterocyclic compounds of our invention are added to the foodstuff, chewing gum or medicinal product as an essential and integral part of a flavoring composition, it is, of course, necessary that the total quantity of flavoring composition employed be sufficient to yield an effective oxathio heterocyclic compound concentration.

Flavoring compositions prepared using the compounds of the present invention, preferably contain the oxathio heterocyclic compound in concentrations ranging from $2 \times 10^{-7}$ up to about 20% by weight, based on the total weight of said flavoring compositions, but may contain as much as 80 or 90% by weight of the oxathio heterocyclic compound if the flavoring composition is then applied in a very small amount.

It will be understood by those skilled in the art that the oxathio heterocyclic compounds of our invention can be added to the foodstuffs to be flavored at any convenient point in the production of the foodstuff, chewing gum, or medicinal product by any of the conventional techniques, including spray-drying, blending, stirring, dissolving and the like. Thus, when they are used to alter or otherwise vary the flavor of a foodstuff the oxathio heterocyclic compounds of our invention can be added in the original mixture, dough, emulsion, batter or the like, prior to any cooking or heating operation. Alternatively, they can be added at a later stage of processing if volatilization losses would be excessive during the earlier processing.

The oxathio heterocyclic compounds or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like. The oxathio heterocyclic compounds according to our invention can be incorporated with the carriers by conventional means such as spray-drying, drum-drying and the like. Such carriers can also include materials for coascervating the oxathio heterocyclic compounds (and other flavoring ingredients, as present) to provide encapsulated products. When a carrier is an emulsion, the flavoring composition can also contain emulsifiers such as mono- and diglycerides or fatty acids and the like. With these carriers or vehicles, the desired physical form of the composition can be prepared.

The following examples are given to illustrate embodiments of the invention as it is now preferred to practice it. It will be understood that these examples are illustrative, and the invention is not to be considered as restricted thereto except as indicated in the appended claims. All parts, proportions, percentages and ratios herein are by weight unless otherwise indicated.

IN THE DRAWINGS

EXAMPLE I

Preparation of 2-methyl-1,3-oxathiolane

Figure 1:
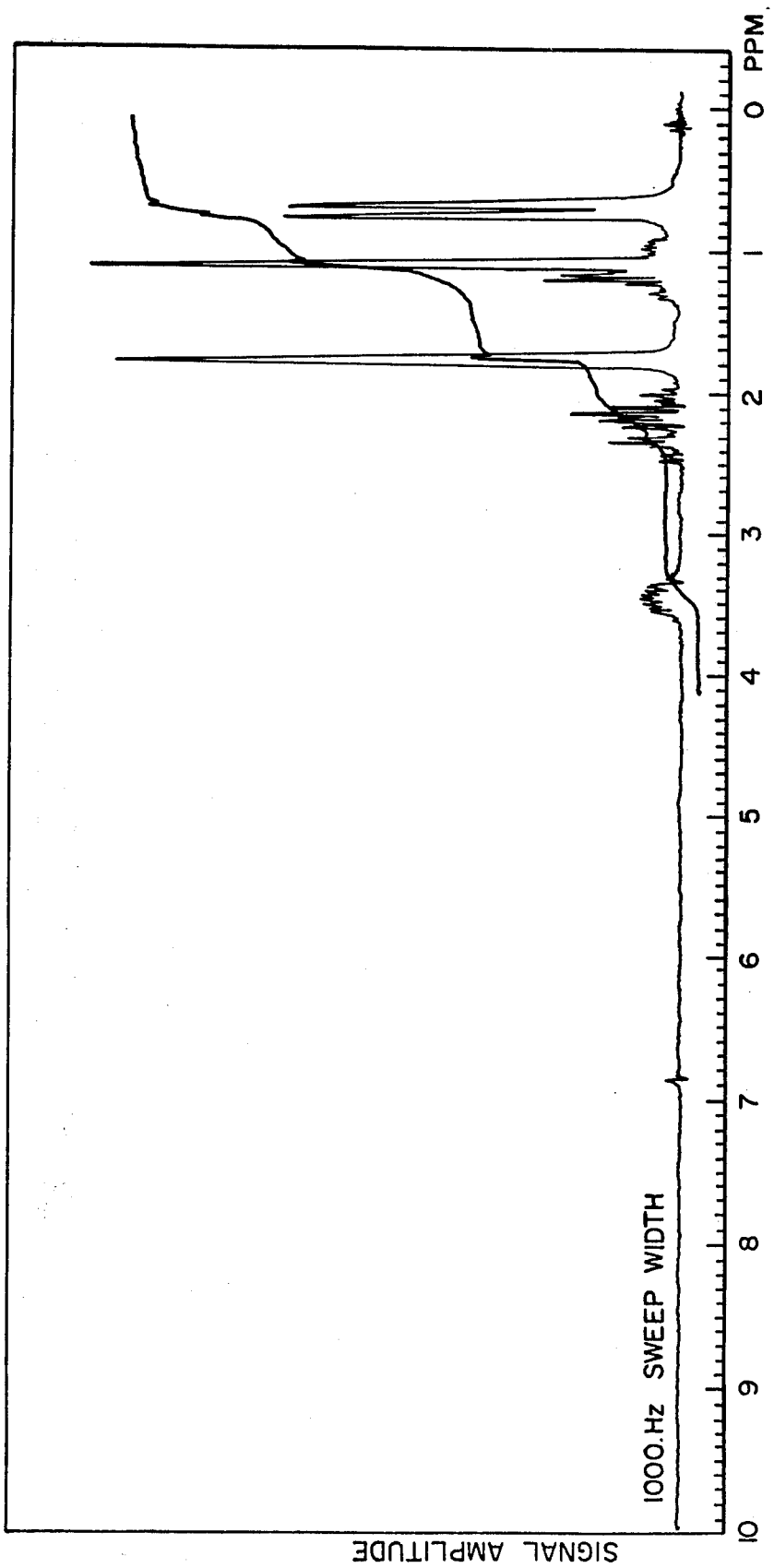
FIG. 1 represents the nuclear magnetic resonance (herein referred to as "NMR") spectrum for 2,6-dimethyl-2-acetyl-1,3-oxathiane, the compound produced according to Example IV.
Figure 2:
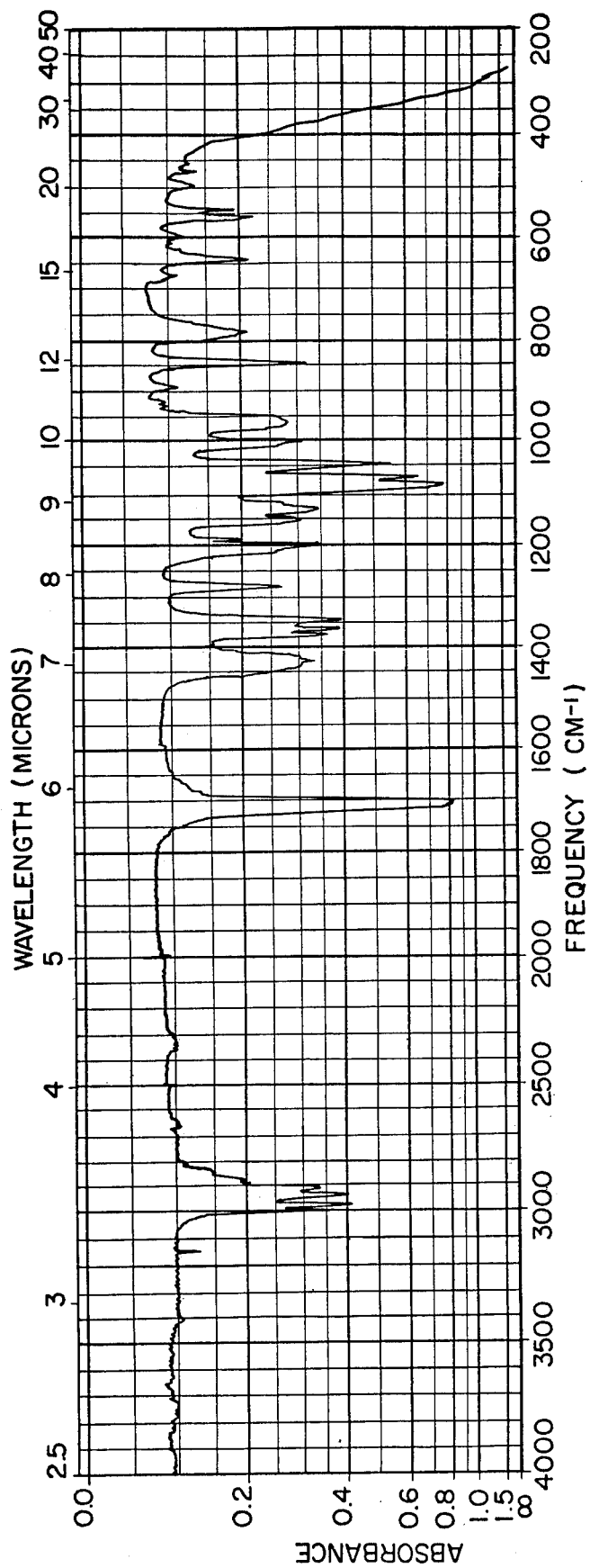
FIG. 2 represents the infra-red (herein after referred to as "IR") spectrum for 2,6-dimethyl-2-acetyl-1,3-oxathiane, the compound produced according to Example IV.
Figure 3:
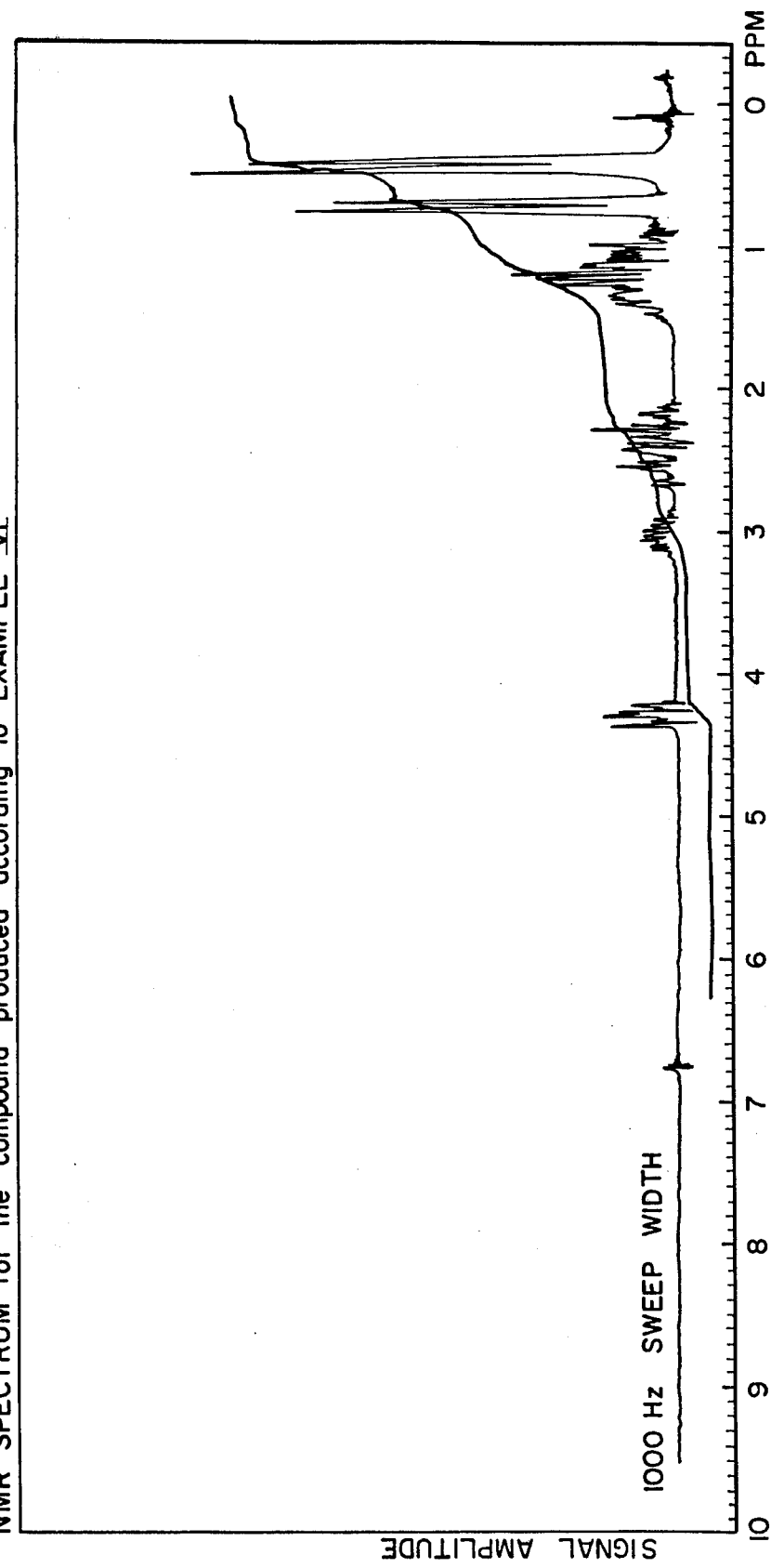
FIG. 3 represents the NMR spectrum for 2-isobutyl-6-methyl-1,3-oxathiane, the compound produced according to Example VI.
Figure 4:
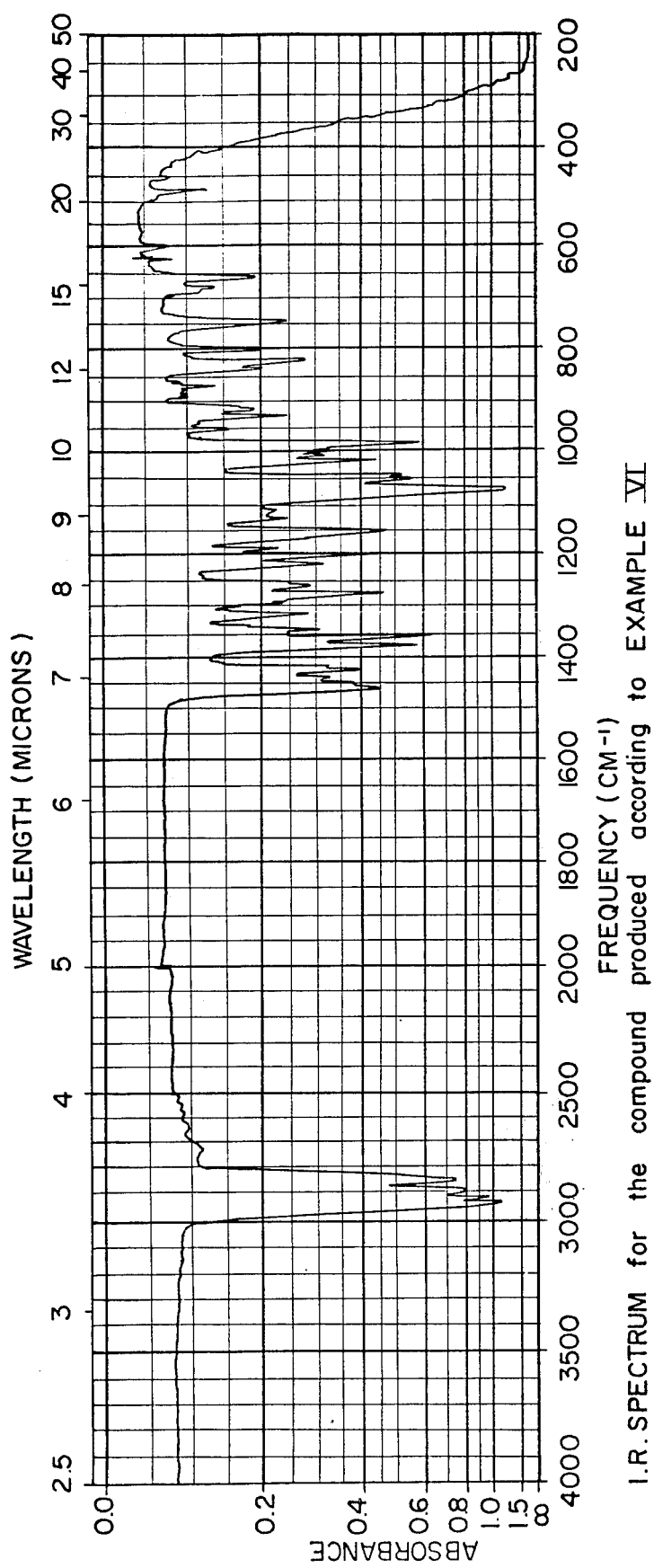
FIG. 4 represents the IR spectrum for 2-isobutyl-6-methyl-1,3-oxathiane, the compound produced according to Example VI.
Figure 5:
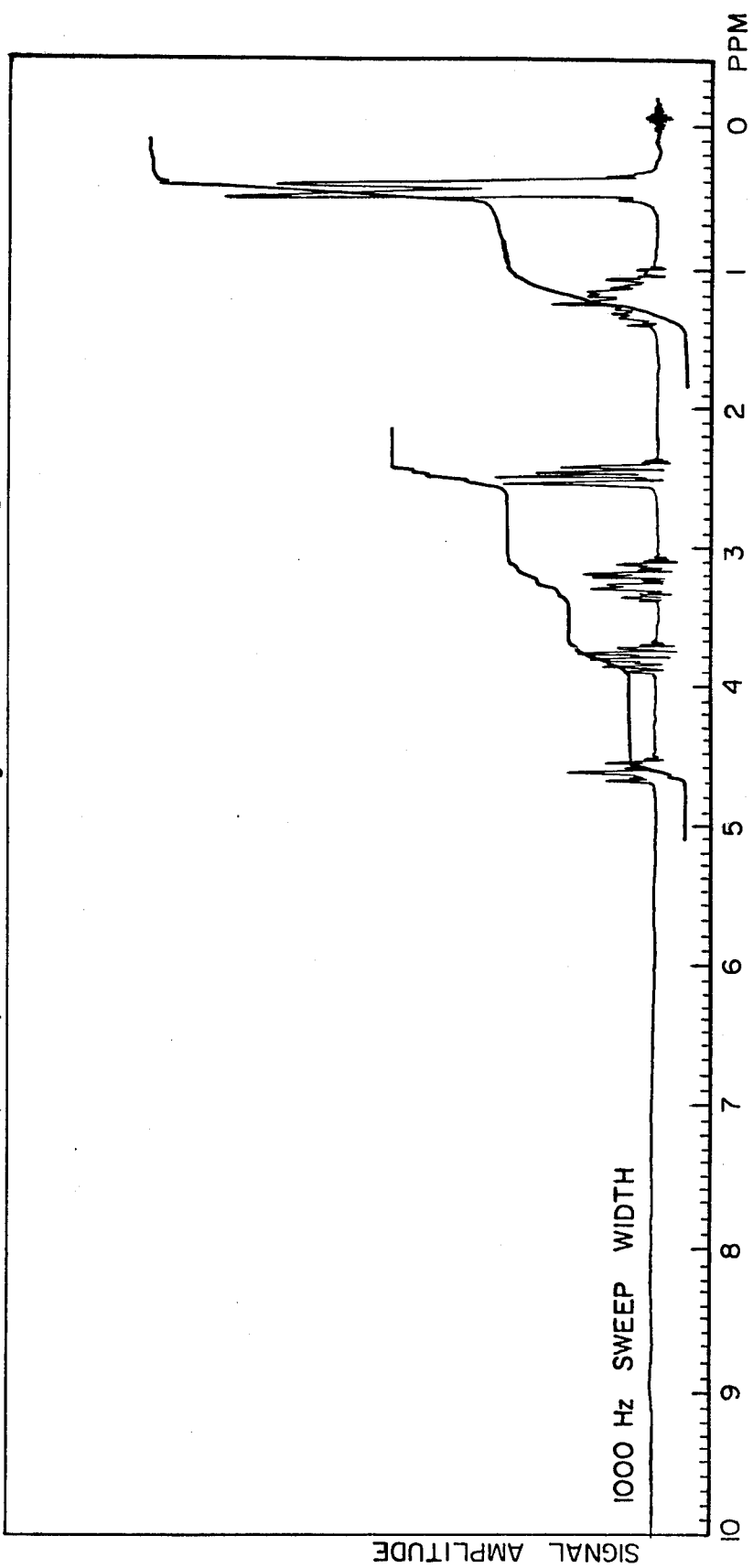
FIG. 5 represents the NMR spectrum for 2;L -isobutyl-1,3-oxathiolane, the compound produced according to Example VIII.
Figure 6:
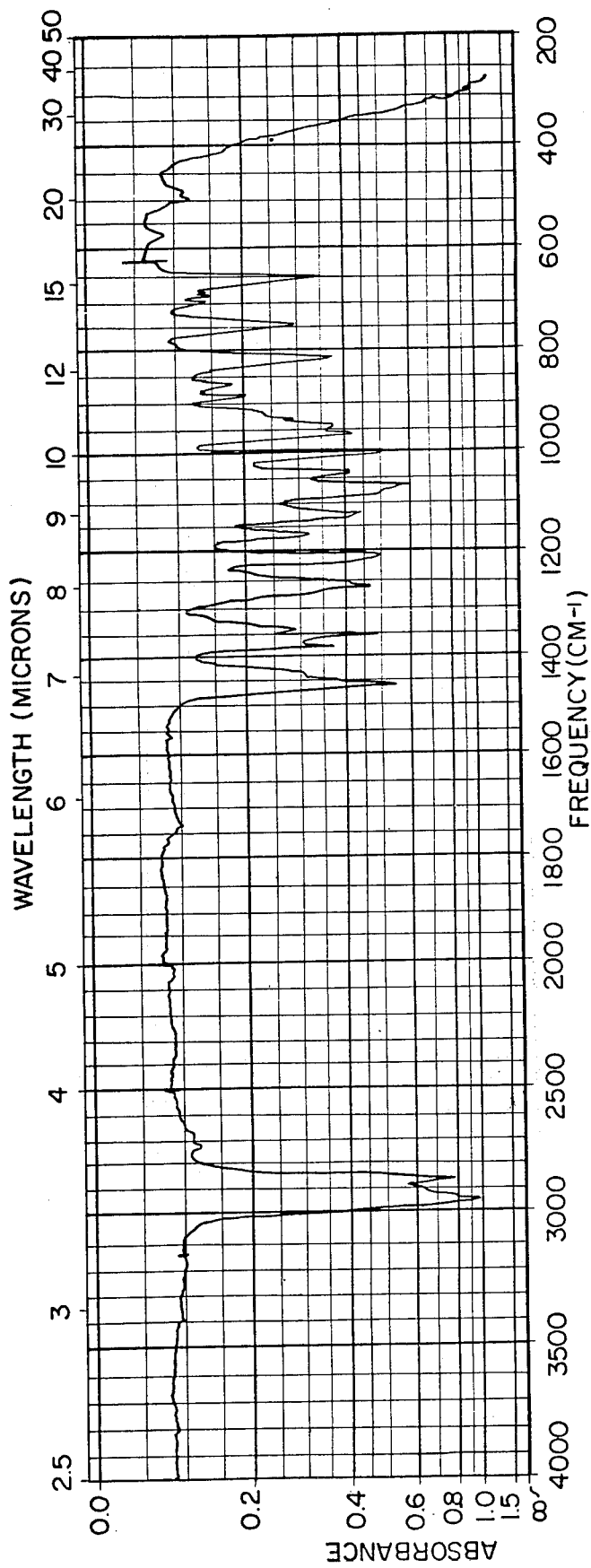
FIG. 6 represents the IR spectrum for 2-isobutyl-1,3-oxathiolane, the compound produced according to Example VIII.
Figure 7:
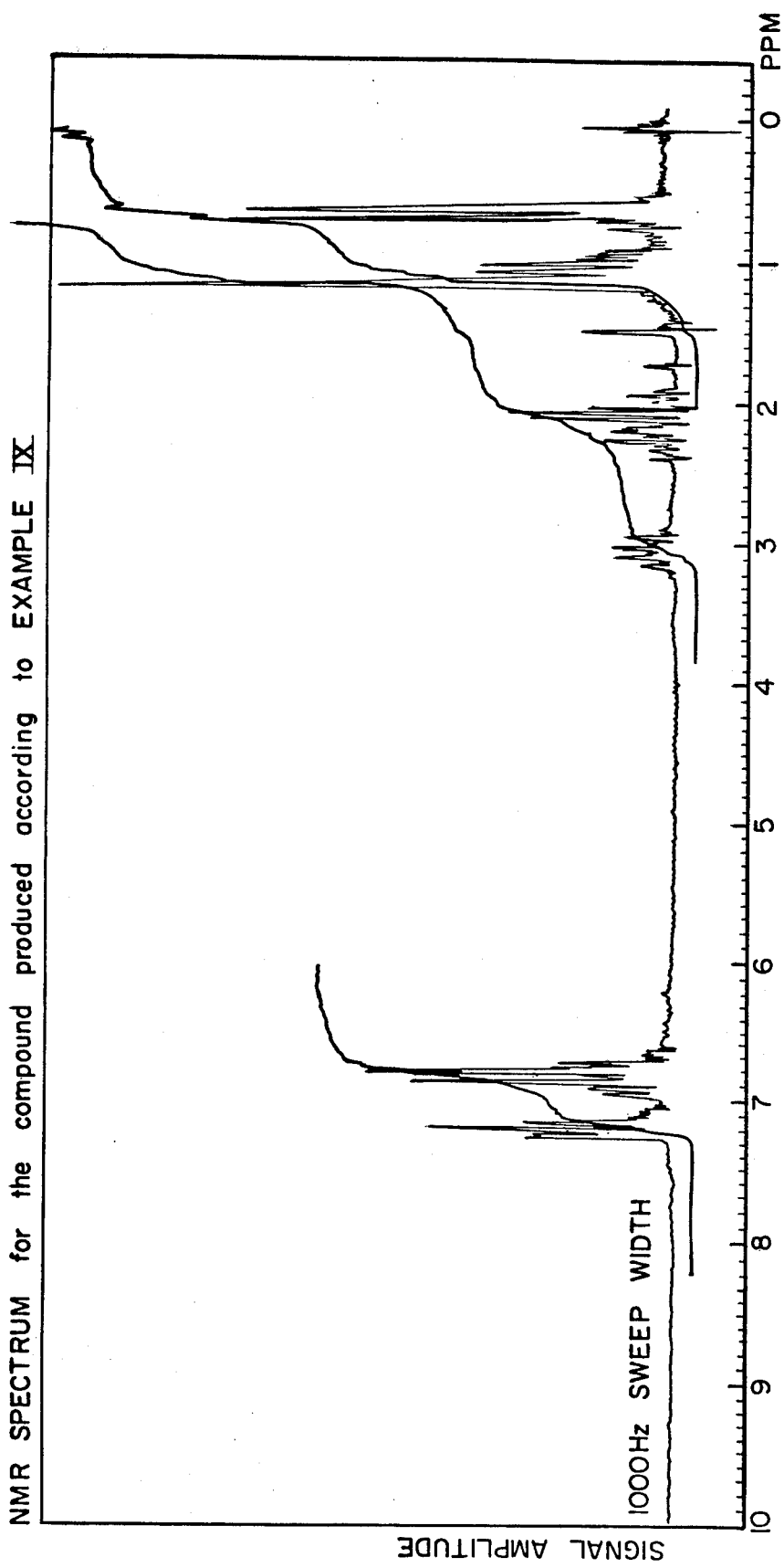
FIG. 7 represents the NMR spectrum for 2,6-dimethyl-2-phenyl-1,3-oxathiane, the compound produced according to Example IX.
Figure 8:
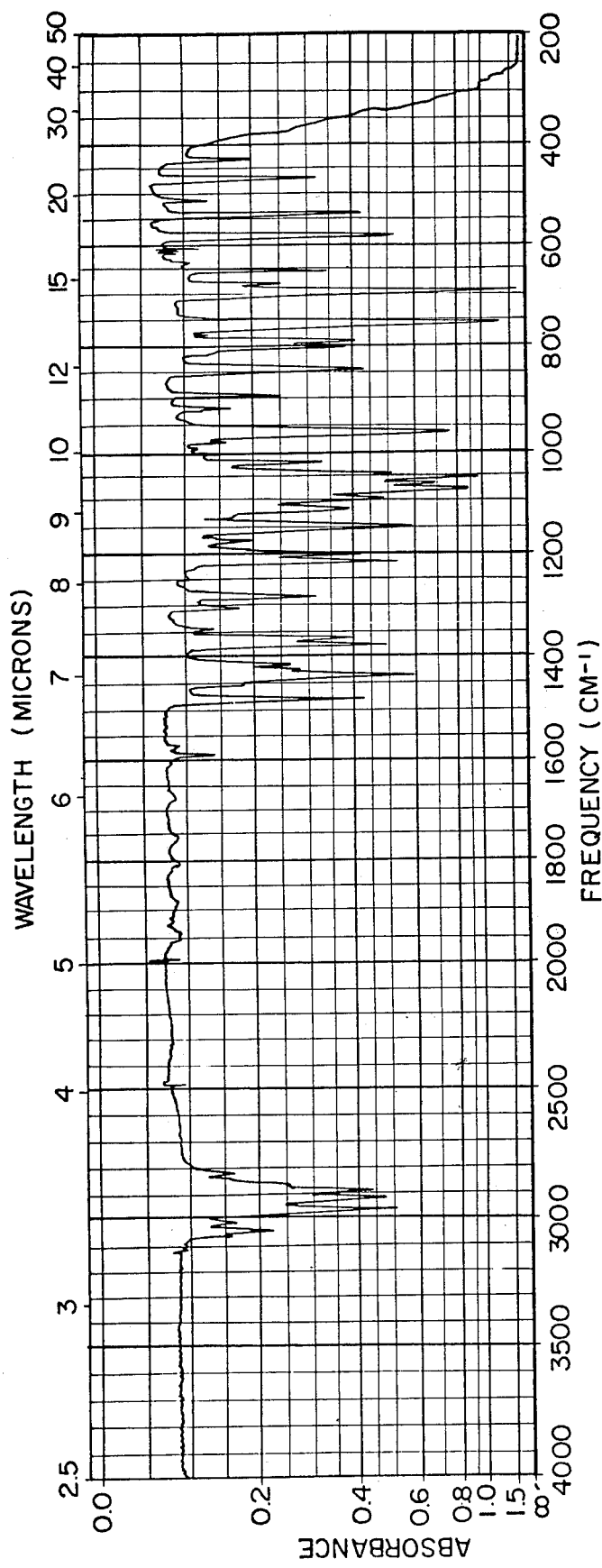
FIG. 8 represents the IR spectrum for 2,6-dimethyl-2-phenyl-1,3-oxathiane, the compound produced according to Example IX.
Figure 9:
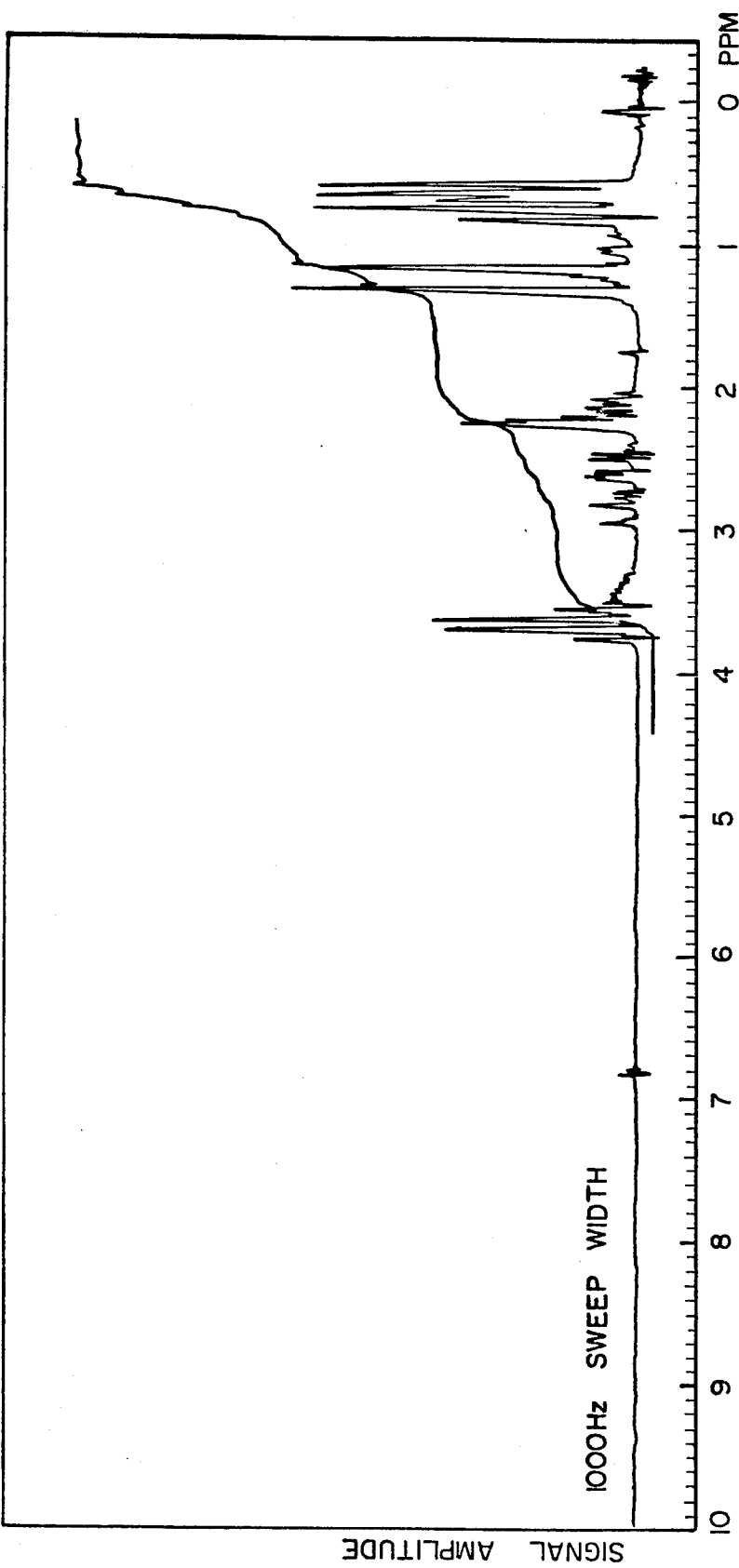
FIG. 9 represents the NMR spectrum for ethyl-2,6-dimethyl-1,3-oxathiane-2-acetate produced according to Example X.
Figure 10:
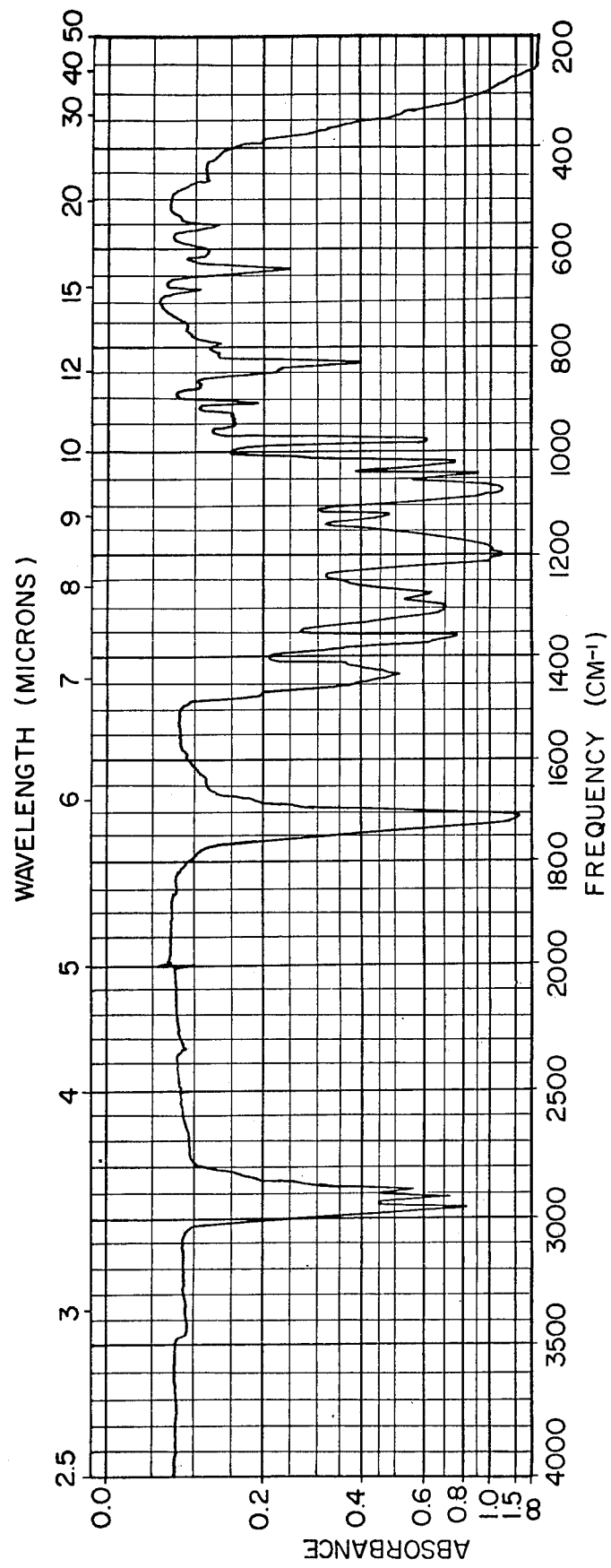
FIG. 10 represents the IR spectrum for ethyl-2,6-dimethyl-1,3-oxathiane-2-acetate produced according to Example X.
Figure 11:
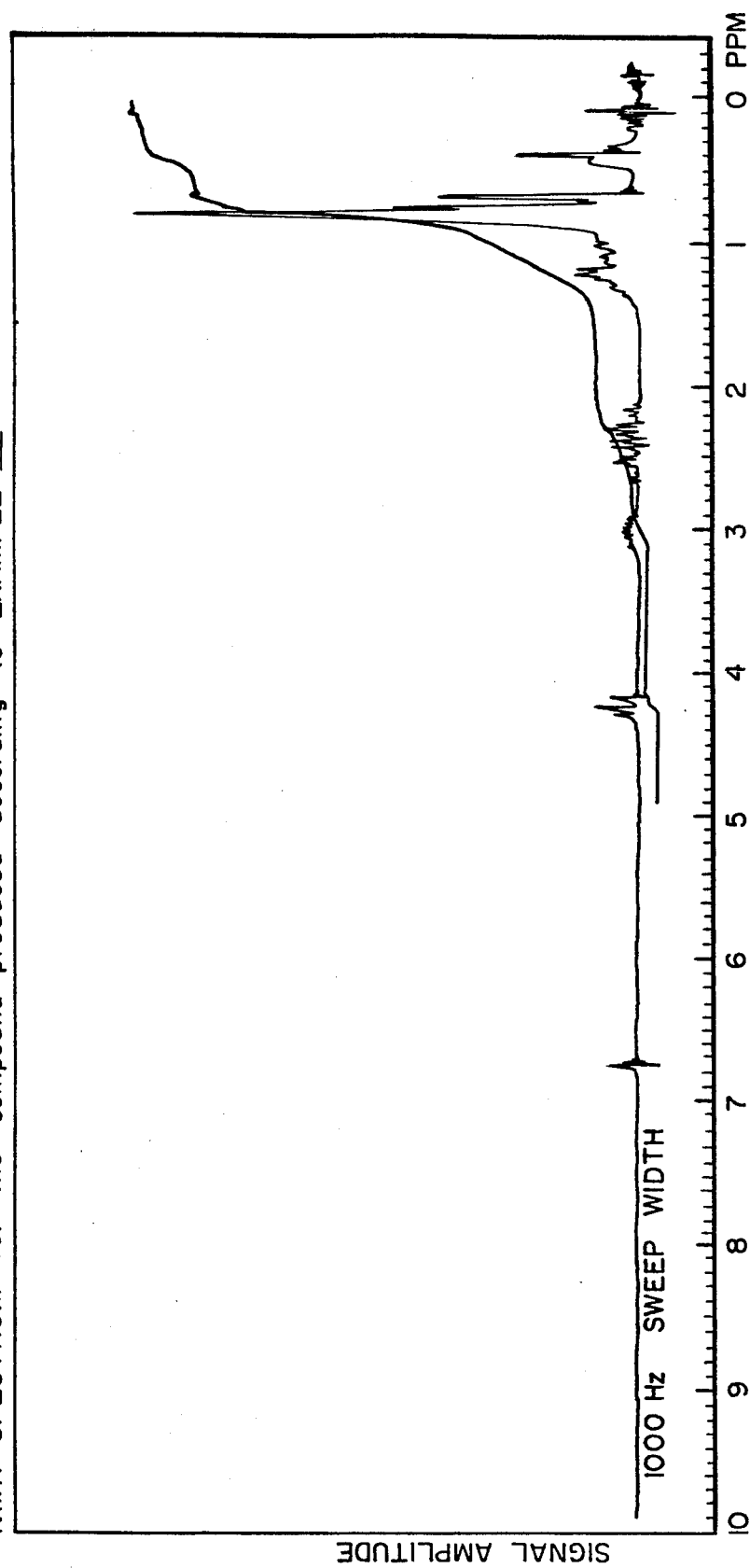
FIG. 11 represents the NMR spectrum for 2-n-nonyl-6-methyl-1,3-oxathiane produced according to Example XI.
Figure 12:
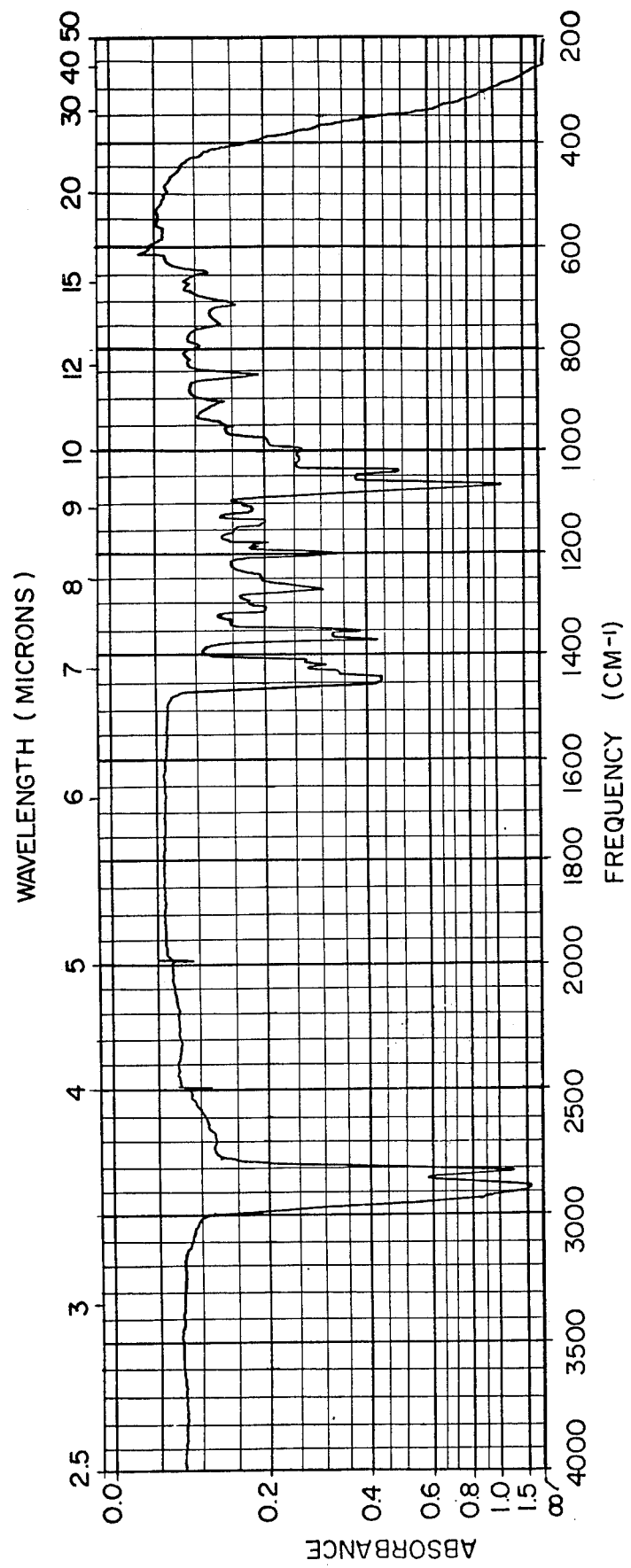
FIG. 12 represents the IR spectrum for 2-n-nonyl-6-methyl-1,3-oxathiane produced according to Example XI.
Figure 13:
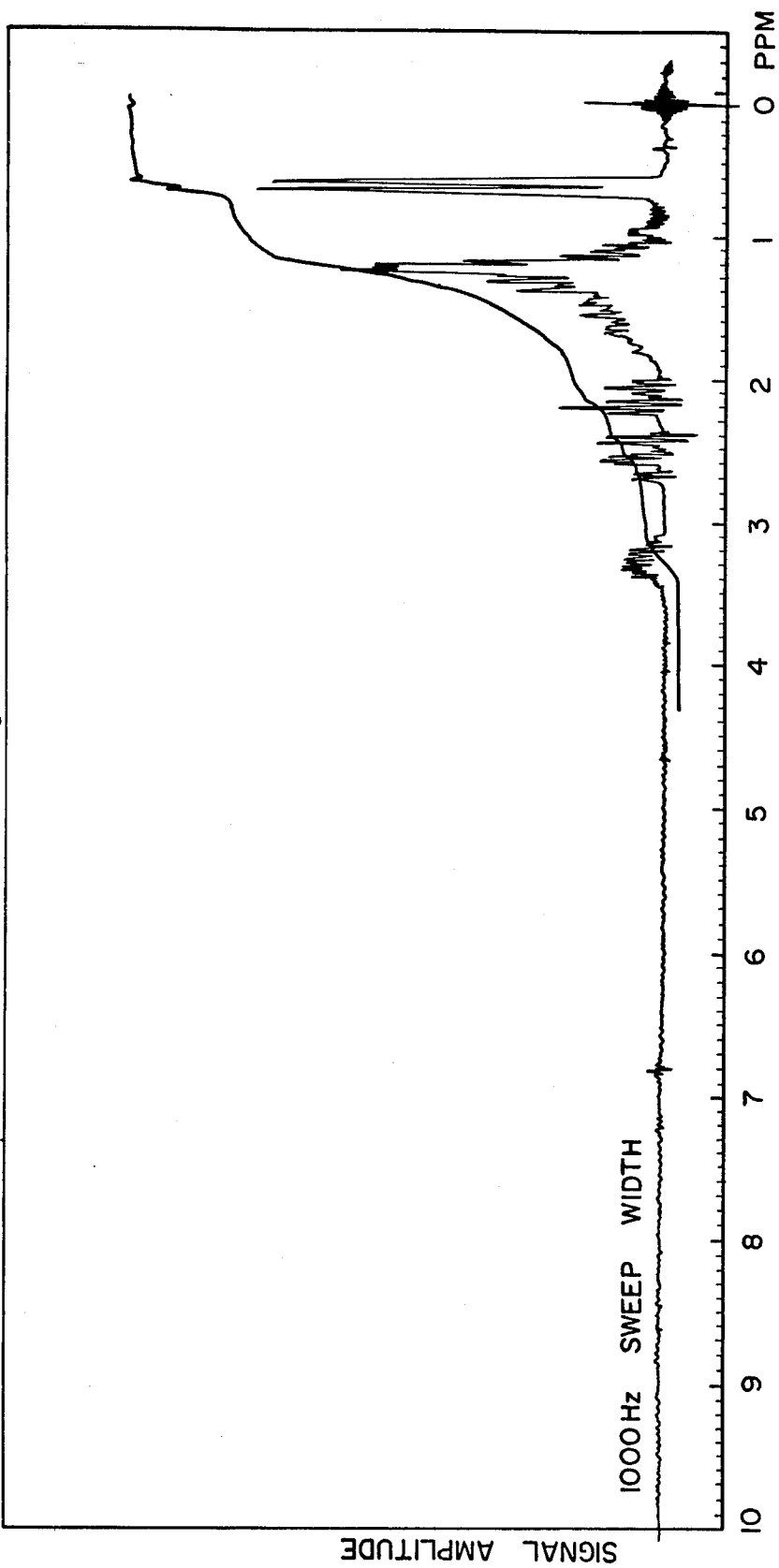
FIG. 13 represents the NMR spectrum for 7-methyl (6-oxa-10-thiaspiro)4.5-decane produced according to Example XII.
Figure 14:
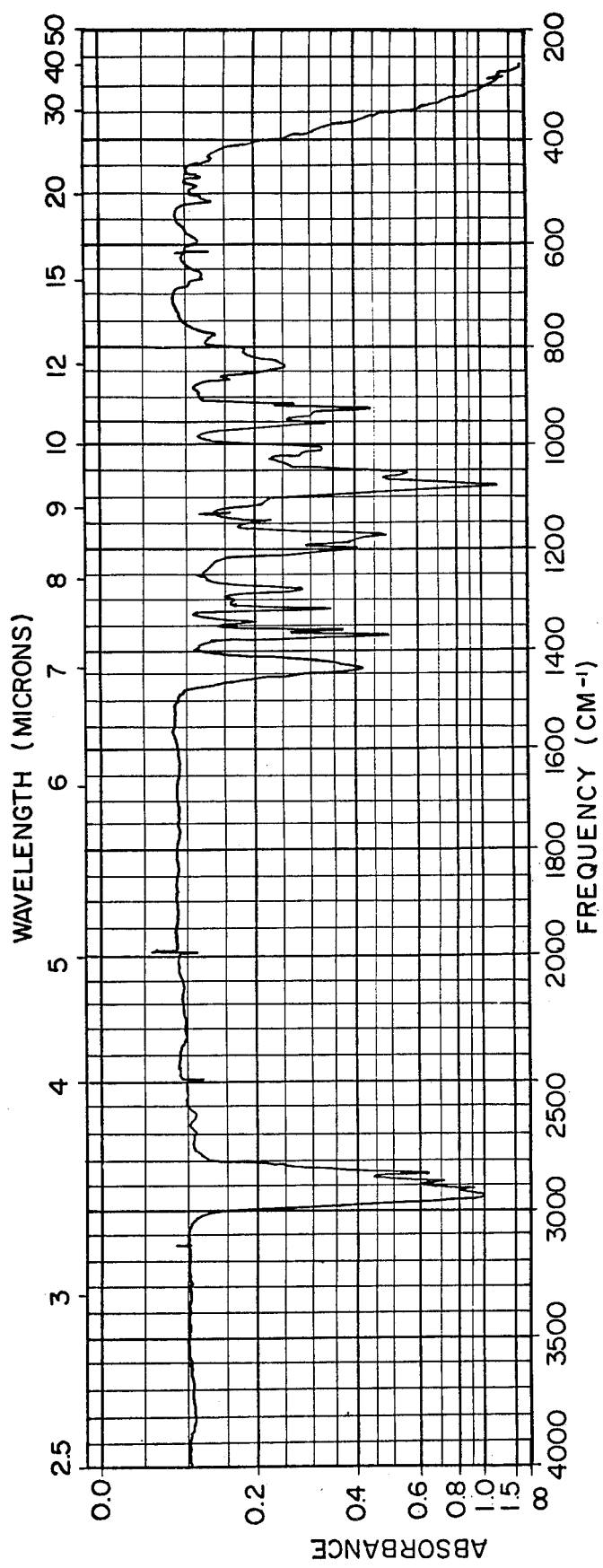
FIG. 14 represents the IR spectrum for 7-methyl(6-oxa-10-thiaspiro)4.5-decane produced according to Example XII.

Reaction:

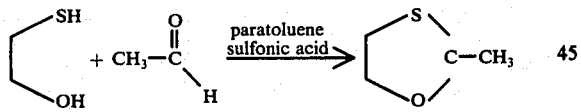

Procedure:

Into a 500 ml round-bottom flask is placed 250 ml dichloromethane. To the dichloromethane is added 39 grams of 2-mercapto ethanol. 24.2 grams of acetaldehyde is then added followed by 0.5 grams of p-toluene sulfonic acid. After boiling chips are added to the flask, a Dean-Starke distilling receiver is placed on the flask, and a reflux condenser is placed on the receiver. The flask is then heated slowly until reflux commences, and then the temperature is increased for a more vigorous reflux. The refluxing takes place over a period of 2½ hours (until water of reaction ceases to be collected).

The reaction mass is then cooled to room temperature and neutralized to a pH of about 8 with diethyl amine. The reaction mass is then filtered through fluted filter paper. The dichloromethane is removed from the reaction mass by means of rotary evaporation. 52.7 grams of crude product is then recovered. The resulting crude product is distilled by means of vacuum distillation, yielding the following fractions:

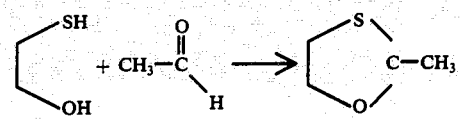

| Fraction No. | Vapor Temp. | Pressure (mm Hg) | Weight of Fraction |
|---|---|---|---|
| 1 | 25-35° C | 20 mm Hg | 2.0 g |
| 2 | 37 | 19 | 5.0 |
| 3 | 35 | 21 | 5.3 |
| 4 | 35 | 21 | 7.4 |
| 5 | 34 | 21 | 6.8 |
| 6 | 34 | 20 | 5.5 |

The resulting material has a sulfury, metallic tomato aroma with a beet-like nuance and a sulfury, garlic, metallic flavor with a celery-like nuance.

NMR, IR and Mass Spectral Analyses confirm that the struture of the resulting product is:

Mass Spectral Analysis:

| m/e | Relative Intensity |
|---|---|
| 26 | 16 |
| 27 | 37[6] |
| 29 | 22 |
| 43 | 30 |
| 45 | 62[2] |
| 59 | 53[4] |
| 60 | 100[1] |
| 61 | 42[5] |
| 89 | 18 |
| 104p | 55[3] |

The NMR Analysis is as follows:

| 1.52 ppm (d) | $CH_3-\overset{H}{\underset{}{C}}\overset{S-}{\underset{O-}{}}$ | 3H |
|---|---|---|
| 3.02 (t) | $CH_2-CH_2-S-$ | 2H |
| 3.72 (m) | | 1H |
| 4.30 (m) | $CH_2-CH_2-O-$ | 1H |
| 5.13 (q) | $Me-\underset{O-}{\overset{H}{\underset{|}{C}}}-S-$ | 1H |

Infrared Analysis is as follows:
660 cm$^{-1}$
855
1045
1095
1130
1215
1260
1270
1380
2870
2930
2950
2980

EXAMPLE II

Preparation of 2,6-Dimethyl-1,3-Oxathiane

Reaction:

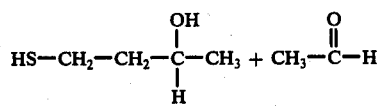

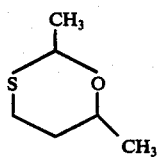

Procedure:

75 ml dichloromethane is placed in a 150 ml round-bottom flask. To the dichloromethane 5.3 grams (0.05 moles) of 4-mercapto-2-butanol is added. 2.42 grams (0.055 moles) of acetaldehyde is then added followed by 0.1 grams of p-toluene sulfonic acid. Boiling chips are added to the flask. A Dean-Starke distilling receiver is placed on the flask, and a reflux condenser is placed on the receiver. The flask is then heated slowly until reflux occurs, and then the temperature is increased for a more vigorous reflux. The reflux lasts approximately two hours before water of reaction ceases to be formed. The reaction mass is then cooled to room temperature and neutralized with diethyl amine to a pH of about 8. The reaction mass is filtered through fluted filter paper, and the dichloromethane is removed by rotary evaporation. The crude product is then distilled by means of vacuum distillation, yielding the following fractions:

| Fraction No. | Vapor Temp. | Pressure (mm Hg) | Purity |
|---|---|---|---|
| 1 | 55–61° C | 20 mm Hg | 97.93% |
| 2 | 61 | 20 | 98.27% |
| 3 | 55 | 20 | 97.50% |

GLC analysis indicates that there still are traces of 4-mercapto-2-butanol in the reaction mass. Accordingly, in order to remove traces of 4-mercapto-2-butanol, the 4-mercapto-2-butanol is re-reacted with acetaldehyde as follows:

75 ml of dichloromethane is placed in a 150 ml round-bottom flask. To this is added 1.0 grams of acetaldehyde, 0.1 grams of p-toluene sulfonic acid and 5.0 grams of 2,6-dimethyl-1,3-oxathiane distillate, containing the 4-mercapto-2-butanol impurity.

Boiling chips are then added to the flask. A Dean-Starke distilling receiver is placed on the flask, and a reflux condenser is placed on the receiver. The flask is then heated slowly until reflux occurs and then the temperature is increased for a more vigorous reflux. The reflux takes place over a period of 2 hours before the water of reaction causes to be formed. The reaction mass is then cooled and neutralized with diethyl amine to a pH of about 8. The reaction mass is then filtered through fluted filter paper, and the dichloromethane solvent is removed by means of rotary evaporation. The resulting reaction product is distilled yielding two fractions:

| Fraction No. | Vapor Temp. | Pressure (mm Hg) | Weight of Fraction | Purity |
|---|---|---|---|---|
| 1 | 54–58° C | 20 mm Hg | 0.6 g | 98.5% |
| 2 | 51 | 20 | 0.9 | 98.4% |

The resulting product is confirmed by NMR, IR and Mass Spectral analyses to have the structure:

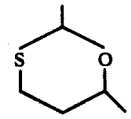

Mass Spectral Analysis is as follows:

| m/e | Relative Intensity |
|---|---|
| 27 | 25 |
| 43 | 40[4] |
| 45 | 32 |
| 46 | 64[3] |
| 47 | 31 |
| 54 | 36[6] |
| 55 | 84[2] |
| 60 | 100[1] |
| 88 | 35 |
| M132 | 40[5] |

NMR Analysis is as follows:

| | | |
|---|---|---|
| 1.18 ppm (d) | $CH_3-\underset{H}{\overset{H}{C}}-O-$ | 3H |
| 1.44 (d) | $CH_3-\underset{O-}{\overset{H}{C}}-S-$ | 3H |
| 1.66 (m) | $-CH_2-$ | 2H |
| 3.14–2.60 (m) | $-CH_2-S-$ | 2H |
| 3.54 (m) | | 1H |
| | $Me-\underset{H}{\overset{}{C}}-O-$ | |
| 4.84 (q) | $\underset{Me-\underset{H}{\overset{}{C}}-S-}{O-}$ | 1H |

IR Analysis is as follows:
660 cm$^{-1}$
845
945
1050
1080
1160
1205
1255
1365
1380
2850
2900
2930
2970

The resulting product has a sweet, fruity, green aroma with an ethyl propionate-like nuance, and a sweet, fruity, berry flavor with green, vegetable, butternut-like, ethyl propionate-like, rum and grapefruit-like nuances.

EXAMPLE III

Preparation of 6-Methyl-2-Phenyl-1,3-Oxathiane

Reaction:

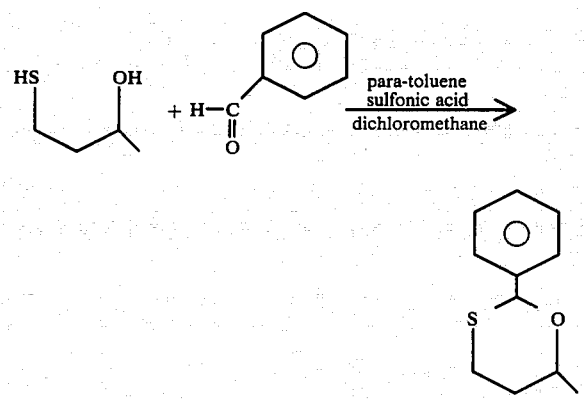

Procedure:

75 ml of dichloromethane is placed into a 100 ml round-bottom flask. To the dichloromethane is added 5.3 grams (0.05 moles) of 4-mercapto-2-butanol. 5.8 grams (0.055 moles) of benzaldehyde is then added followed by 0.1 grams of p-toluene sulfonic acid. Boiling chips are added to the flask. A Dean-Starke distilling receiver is placed on the flask, and a reflux condenser is placed on the receiver. The flask is then heated slowly until reflux occurs, and then the temperature is increased for a more vigorous reflux. The reflux lasts for a period of 2 hours before water of reaction ceases to be formed. The reaction mass is then cooled and neutralized with diethyl amine to a pH of 8. The reaction mass is filtered through fluted filter paper, and the dichloromethane solvent is removed by means of rotary evaporation. 10.1 grams of crude product are recovered after the rotary evaporation operation. The crude product is then distilled by means of vacuum distillation yielding the following 3 fractions:

| Fraction No. | Vapor Temp. | Pressure (mm Hg) | Weight of Fraction | Purity |
|---|---|---|---|---|
| 1 | 31-95° C | 5 mm Hg | — | — |
| 2 | 97 | 0.25 | — | — |
| 3 | 99 | 0.25 | 7.7 g | 99.88% |

NMR, IR and Mass Spectral analyses yield the information that the resulting reaction product is:

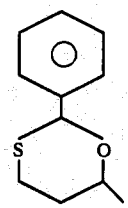

Mass Spectral Analysis is as follows:

| m/e | Relative Intensity |
|---|---|
| 27 | 44 |
| 45 | 44 |
| 46 | 59 |
| 55 | 77[3] |
| 60 | 90[2] |
| 77 | 63[6] |
| 83 | 100[1] |
| 105 | 47 |
| 107 | 73[5] |
| M194 | 74[4] |

NMR Analysis is as follows:

| 1.28 ppm | $CH_3-\overset{H}{\underset{|}{C}}-O-$ | 3H |
|---|---|---|
| 1.75 (m) | $-CH_2-$ | 2H |
| 3.32-2.68 (m) | $-CH_2-S-$ | 2H |
| 3.70 (m) | $Me-\overset{H}{\underset{|}{C}}-O$ | 1H |
| 5.82 (s) | Phenyl$-\overset{S-}{\underset{H}{\overset{|}{C}}}{\diagdown}_{O-}$ | 1H |
| 7.40 (m) | Aryl protons | 5H |

IR Analysis is as follows:
690 cm$^{-1}$
700
880
1000
1020
1030
1050
1080
1135
1250
1230
1275
1360
1375
1445
2840
2890
2920
2960

The resulting product has a roasted sulfury aroma with almond and coffee-like nuances and a roasted meat-like, roasted sulfury taste.

EXAMPLE IV

Preparation of 2,6-Dimethyl-2-Acetyl-1,3-Oxathiane

Reaction:

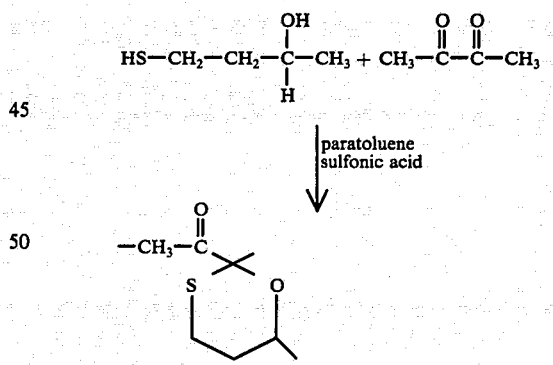

Procedure:

75 ml of dichloromethane is placed into a 100 ml round-bottom flask. To the dichloromethane is added 5.3 grams (0.05 moles) of 4-mercapto-2-butanol. 4.7 grams (0.055 moles) of diacetyl is then added followed by 0.1 grams of p-toluene sulfonic acid. Boiling chips are added to the flask. A Dean-Starke distilling receiver is placed on the flask, and a reflux condenser is placed on the receiver. The flask is then heated slowly until reflux occurs, and then the temperature is increased for a more vigorous reflux. The reflux lasts for a period of 2 hours before water of reaction ceases to be formed. The reaction mass is then cooled and neutralized with diethyl amine to a pH of about 8. The reaction mass is filtered through fluted filter paper, and the dichloromethane solvent is removed by means of rotary evaporation. 9.5 grams of crude product are recovered after the rotary evaporation operation. The crude product is then distilled by means of vacuum distillation yielding the following 4 fractions:

| Fraction No. | Vapor Temp. | Pressure (mm Hg) | Weight of Fraction |
|---|---|---|---|
| 1 | 36–45° C | 0.075 | 1.8 |
| 2 | 52 | 0.075 | 2.1 |
| 3 | 52 | 0.25 | 2.7 |
| 4 | 45 | 0.20 | 0.5 |

NMR, IR and Mass Spectral analyses yield the information that the resulting reaction product is:

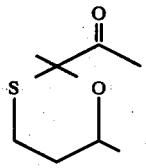

Mass spectral analysis is as follows:

| m/e | Relative Intensity |
|---|---|
| 27 | 13[5] |
| 29 | 6 |
| 39 | 7 |
| 43 | 100[1] |
| 45 | 8 |
| 47 | 9 |
| 55 | 30[4] |
| 59 | 12[6] |
| 89 | 31[3] |
| 131 | 45[2] |
| M174 | 0 |

NMR Analysis is as follows:

| 1.18 ppm (t) | H<br>\|<br>CH$_3$—C—O— | 3H |
|---|---|---|
| 1.56 (s) | \|<br>C=O<br>\|<br>CH$_3$—C—O—<br>\|<br>S— | 3H |
| 1.74 (m) | —CH$_2$— | 2H |
| 2.25 (s) | CH$_3$—C—<br>‖<br>O | 3H |
| 2.77–2.46 (m) | —CH$_2$—S— | 2H |
| 3.74 (m) | H<br>\|<br>Me—C—O— | 1H |

Infra-Red Analysis is as follows:
845 cm$^{-1}$
1050
1075
1090
1130
1150
1205
1350
1365
1380
1430
1710
1720
2910
2930
2980

The resultant compound has a sweet, meaty/sulfury, metallic aroma and taste with a "burning sensation" effect.

EXAMPLE V

Preparation of 2,2,6-Trimethyl-1,3-Oxathiane

Reaction:

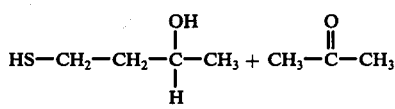

Procedure:
75 ml of dichloromethane is placed into a 100 ml round-bottom flask. To the dichloromethane is added 5.3 grams (0.05 moles) of 4-mercapto-2-butanol. 3.2 grams (0.055 moles) of acetone is then added followed by 0.1 grams of p-toluene sulfonic acid. Boiling chips are added to the flask. A Dean-Starke distilling receiver is placed on the flask, and a reflux condenser is placed on the receiver. The flask is then heated slowly until reflux occurs, and then the temperature is increased for a more vigorous reflux. The reflux lasts for a period of 2 hours before water of reaction ceases to be formed. The reaction mass is then cooled and neutralized with diethyl amine to a pH of about 8. The reaction mass is filtered through fluted filter paper, and the dichloromethane solvent is removed by means of rotary evaporation. 7.2 grams of crude product are recovered after the rotary evaporation operation. The crude product is then distilled by means of vacuum distillation yielding the following 3 fractions:

| Fraction No. | Vapor Temp. | Pressure (mm Hg) | Weight of Fraction | Purity |
|---|---|---|---|---|
| 1 | 38–51° C | 11 | 0.95 g | 99.48% |
| 2 | 51 | 11 | 2.2 | 98.87% |
| 3 | 42 | 11 | 1.3 | 99.97% |

NMR, IR and Mass Spectral analyses yield the information that the resulting reaction product is:

Mass Spectral Analysis is as follows:

| m/e | Relative Intensity |
|---|---|
| 27 | 43 |
| 39 | 34 |
| 43 | 67[4] |
| 45 | 35 |
| 46 | 50[6] |
| 55 | 69[3] |

-continued

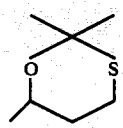

Mass Spectral Analysis is as follows:

| m/e | Relative Intensity |
|---|---|
| 59 | 100[1] |
| 60 | 70[2] |
| 88 | 59[5] |
| M146 | 35 |

NMR Analysis is as follows:

| 1.13 ppm (d) | $CH_3\text{—}\underset{\underset{H}{\mid}}{C}\text{—O—}$ | 3H |
|---|---|---|
| 1.51 (s) | $CH_3\text{—}\underset{\underset{S\text{—}}{\mid}}{\overset{\overset{CH_3}{\mid}}{C}}\text{—O—}$ | 3H |
| 1.65 (s) | $CH_3\text{—}\underset{\underset{S\text{—}}{\mid}}{\overset{\overset{CH_3}{\mid}}{C}}\text{—O—}$ | 3H |
| 1.86–1.37 (m) | $\text{—}CH_2\text{—}\underset{\mid}{\overset{H}{C}}\text{—}$ | 2H |
| 3.10 (m) | HC—S— | 1H |
| 2.68, 2.54 (m) | HC—S— | 1H |
| 3.86 (m) | $Me\text{—}\underset{\mid}{\overset{H}{C}}\text{—O—}$ | 1H |

IR Analysis is as follows:
600 cm$^{-1}$
790
825
985
1055
1080
1120
1145
1175
1220
1285
1365
1375
2870
2900
2930
2970

This material has a black-pepper-like, green, spicy aroma with a vegetable-like nuance and a black-pepper-like, spicy, green vegetable-like flavor with cucumber, burning and parsley nuances.

EXAMPLE VI

Preparation of 2-Isobutyl-6-Methyl-1,3-Oxathiane

Reaction:

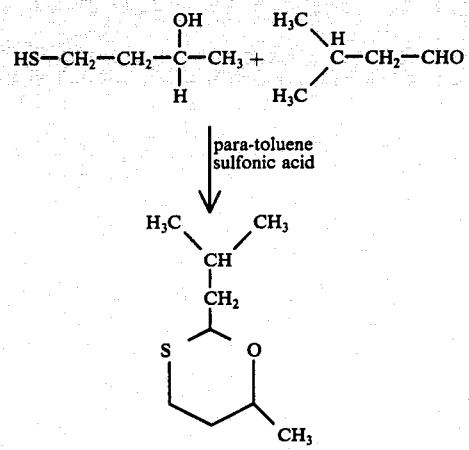

Procedure:

75 ml of dichloromethane is placed into a 100 ml roundbottom flask. To the dichloromethane is added 5.3 grams (0.05 moles) of 4-mercapto-2-butanol. 4.74 grams (0.055 moles) of isovaleraldehyde is then added followed by 0.1 grams of p-toluene sulfonic acid. Boiling chips are added to the flask. A Dean-Starke distilling receiver is placed on the flask, and a reflux condenser is placed on the receiver. The flask is then heated slowly until reflux occurs, and then the temperature is increased for a more vigorous reflux. The reflux lasts for a period of 2 hours before water of reaction ceases to be formed. The reaction mass is then cooled and neutralized with diethyl amine to a pH of about 8. The reaction mass is filtered through fluted filter paper, and the dichloromethane solvent is removed by means of rotary evaporation. 8.8 grams of crude product are recovered after the rotary evaporation operation. The crude product is then distilled by means of vacuum distillation yielding the following 3 fractions:

| Fraction No. | Vapor Temp. | Pressure (mm Hg) | Weight of Fraction | Purity |
|---|---|---|---|---|
| 1 | 37–50° C | 7 | 0.2 g | 85.14% |
| 2 | 59 | 7 | 1.2 | 95.97% |
| 3 | 45 | 7 | 1.6 | 97.91% |

NMR, IR and Mass Spectral analyses yield the information that the resulting reaction product is:

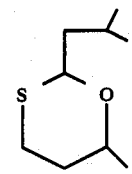

Mass Spectral Analysis is as follows:

| m/e | Relative Intensity |
|---|---|
| 27 | 53[4] |
| 29 | 33 |
| 39 | 29 |
| 41 | 46[5] |
| 43 | 36 |
| 45 | 35 |
| 46 | 39[6] |
| 47 | 36 |
| 55 | 85[2] |
| 60 | 65[3] |
| 117 | 100[1] |

-continued

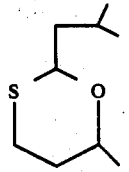

Mass Spectral Analysis is as follows:

| m/e | Relative Intensity |
|---|---|
| M174 | 20 |

NMR Analysis is as follows:

| 0.88 ppm (d) | CH₃\H C— / CH₃ | 6H |
| 1.18 (d) | H \| CH₃—C—O— \| | 3H |
| 2.02–1.40 (m) | H \| —CH₂—C—O— + CH₂— + Me\H C— / Me | 5H |
| 3.02 (m) | HC—S— | 1H |
| 2.78, 2.65 (m) | HC—S— | 1H |
| 4.78 (t) | H \| —CH₂—C—S— \| O— | 1H |
| 3.50 (m) | H \| —C—O \| Me | 1H |

IR Analysis is as follows:
985 cm⁻¹
1020
1050
1060
1080
1155
1200
1280
1365
1385
1430
1455
1465
2860
2900
2920
2950

This material has a spicy, vegetable-like, cantelope aroma with green, fig and rum nuances, and a spice, vegetable, cantelope-like flavor with parsley, "tropical fruit"-like, quince, and burning nuances.

EXAMPLE VII

Preparation of 2,2-Dimethyl-1,3-Oxathiolane

Reaction:

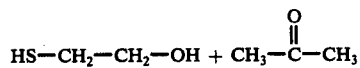

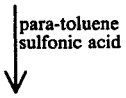

Procedure:

Into a 500 ml round-bottom flask is placed 250 ml dichloromethane. To the dichloromethane is added 39 grams of 2-mercapto ethanol. 31.9 grams of acetone is then added followed by 0.5 grams of p-toluene sulfonic acid. After boiling chips are added to the flask, a Dean-Starke distilling receiver is placed on the flask, and a reflux condenser is placed on the receiver. The flask is then heated slowly until reflux commences, and then the temperature is increased for a more vigorous reflux. The refluxing takes place over a period of 2½ hours (until water of reaction ceases to be formed).

The reaction mass is then cooled to room temperature and neutralized to a pH of about 8 with diethyl amine. The reaction mass is then filtered through fluted filter paper. The dichloromethane is removed from the reaction mass by means of rotary evaporation. 54.5 grams of crude product is then recovered. The resulting crude product is distilled by means of vacuum distillation, yielding the following fractions:

| Fraction No. | Vapor Temp. | Pressure (mm Hg) | Weight of Fraction | Purity |
|---|---|---|---|---|
| 1 | 43–53° C | 43 | 6.7 g | 98.43% |
| 2 | 54 | 43 | 15.1 | 98.83% |
| 3 | 53 | 43 | 5.3 | 99.86% |
| 4 | 54 | 43 | 4.2 | 99.88% |
| 5 | 51 | 43 | 3.4 | 99.75% |

NMR, IR and Mass Spectral Analyses confirm that the structure of the resulting product is:

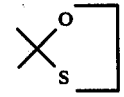

Mass Spectral Analysis:

| m/e | Relative Intensity |
|---|---|
| 27 | 18[6] |
| 39 | 13 |
| 41 | 10 |
| 43 | 54[2] |
| 45 | 29[5] |
| 58 | 10 |
| 59 | 43[3] |
| 60 | 100[1] |
| 61 | 12 |
| 103 | 9 |
| M118 | 30[4] |

NMR Analysis is as follows:

| | | |
|---|---|---|
| 1.58 ppm (s) | CH₃\C/S— , CH₃/ \O— | 6H |
| 3.07 (t) | CH₂—CH₂—S— | 2H |
| 4.12 (t) | CH₂—CH₂—O— | 2H |

IR Analysis is as follows:
805 cm⁻¹
1030
1120
1160
1180
1190
1225
1265
1365
1380
2870
2930
2970

This material has a sulfury, garlic and tomato aroma with a sulfury, garlic and metallic flavor with a strong tomato nuance.

EXAMPLE VIII

Preparation of 2-Isobutyl-1,3-Oxathiolane

Reaction:

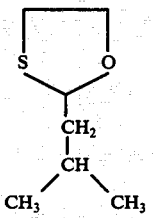

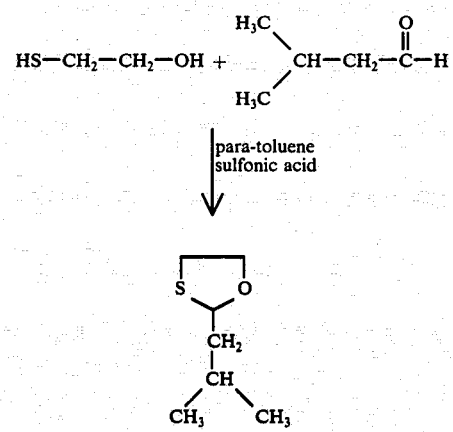

Procedure:

Into a 500 ml round-bottom flask is placed 250 ml dichloromethane. To the dichloromethane is added 39 grams of 2-mercapto ethanol. 47.4 grams of isovaleraldehyde is then added followed by 0.5 grams of p-toluene sulfonic acid. After boiling chips are added to the flask, a Dean-Starke distilling receiver is placed on the flask, and a reflux condenser is placed on the receiver. The flask is then heated slowly until reflux commences, and then the temperature is increased for a more vigorous reflux. The refluxing takes place over a period of 2½ hours (until water of reaction ceases to be formed).

The reaction mass is then cooled to room temperature and neutralized to a pH of about 8 with diethyl amine. The reaction mass is then filtered through fluted filter paper. The dichloromethane is removed from the reaction mass by means of rotary evaporation. 79.4 grams of crude product is then recovered. The resulting crude product is distilled by means of vacuum distillation, yielding the following fractions:

| Fraction No. | Vapor Temp. | Pressure (mm Hg) | Weight of Fraction | Purity |
|---|---|---|---|---|
| 1 | 25–60° C | 20 | 3.9 | 81% |
| 2 | 52 | 4.5 | 6.0 | 95.14% |
| 3 | 52 | 5 | 5.3 | 96.15% |
| 4 | 52 | 5 | 7.2 | 97.40% |
| 5 | 52 | 5 | 7.8 | 98.45% |
| 6 | 52 | 5 | 12.0 | 99.11% |
| 7 | 52 | 5 | 10.7 | 99.48% |
| 8 | 52 | 5 | 5.8 | 99.17% |

NMR, IR and Mass Spectral Analyses confirm that the structure of the resulting product is:

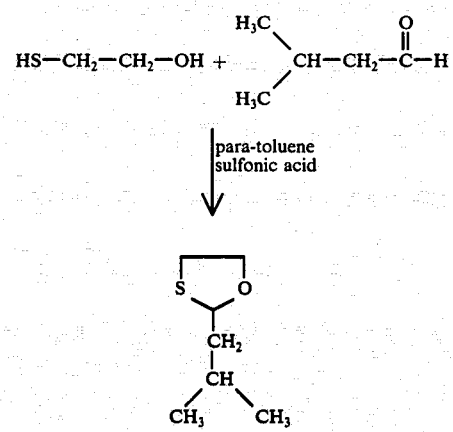

Mass Spectral Analysis is as follows:

| m/e | Relative Intensity |
|---|---|
| 27 | 34[4] |
| 39 | 15 |
| 41 | 21[6] |
| 43 | 14 |
| 45 | 20 |
| 59 | 16 |
| 60 | 53[2] |
| 61 | 50[3] |
| 89 | 100[1] |
| M146 | 24[5] |

NMR Analysis is as follows:

| | | |
|---|---|---|
| 0.93 ppm (d) | CH₃\ H \C— , CH₃/ | 6H |
| 1.72 (m) | —CH₂— + HC— | 3H |
| 2.98 (m) | —CH₂—S— | 2H |
| 3.74 (m) | —CH₂—O— | 1H |
| 4.30 (m) | | 1H |
| 5.10 (t) | CH₂—C—S— , H, O— | 1H |

IR Analysis is as follows:
660 cm⁻¹
820 cm⁻¹
950
965
1010
1045
1070
1085
1125
1130
1205
1310
1320
1365
1380

1460
1465
2880
2900
2930
2950

This material has a horseradish aroma and a horseradish, watercress, leek flavor with a burning nuance.

EXAMPLE IX

Preparation of 2,6-Dimethyl-2-Phenyl-1,3-Oxathiane

Reaction:

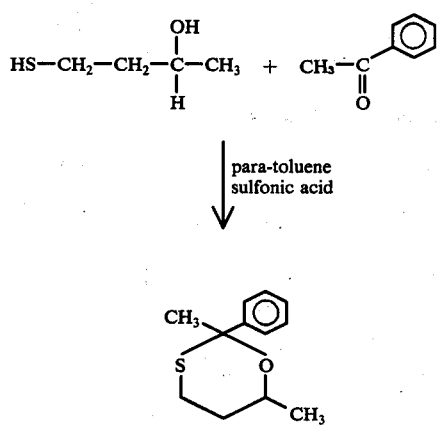

Procedure:

74 ml of dichloromethane is placed into a 100 ml round-bottom flask. To the dichloromethane is added 5.3 grams (0.05 moles) of 4-mercapto-2-butanol. 6.6 grams (0.055 moles) of acetophenone is then added followed by 0.1 grams of p-toluene sulfonic acid. Boiling chips are added to the flask. A Dean-Starke distilling receiver is placed on the flask, and a reflux condenser is placed on the receiver. The flask is then heated slowly until reflux occurs, and then the temperature is increased for a more vigorous reflux. The refluxing lasts for a period of 3 hours before water of reaction ceases to be formed. The reaction mass is then cooled and neutralized with 10% aqueous sodium bicarbonate to a pH of 8. The reaction mass is filtered through fluted filter paper, and the dichloromethane solvent is removed by means of rotary evaporation. 10.4 grams of crude product are recovered after the rotary evaporation operation. The crude product is then distilled by means of vacuum distillation yielding the following 3 fractions:

| Fraction No. | Vapor Temp. | Pressure (mm Hg) | Weight of Fraction |
| --- | --- | --- | --- |
| 1 | 30–32° C | 0.3 | 0.5 |
| 2 | 82 | 0.3 | 2.0 |
| 3 | 83 | 0.3 | — |

NMR, IR and Mass Spectral analyses yield the information that the resulting reaction product is:

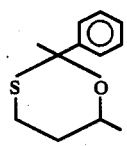

NMR Analysis is as follows:

| | | |
| --- | --- | --- |
| 1.12 ppm (d) | CH$_3$—C—O— H | 3H |
| 1.58 (m) | —CH$_2$—C(H)(CH$_3$)—O— | |
| 1.62 (s) | (phenyl) CH$_3$—C(—S—)(—O—) | 5H |
| 2.92–2.38 (m) | —CH$_2$—S— | 2H |
| 3.54 (g) | Me—C(H)—O— | 1H |
| 7.30 (m) | aromatic H (C—O—, S—) | 3H |
| 7.66 (m) | aromatic H (C—O—, S—) | 2H |

IR Analysis is as follows:

540 cm$^{-1}$
585
700
760
790
840
965
1045
1055
1070
1075
1095
1150
1200
1215
1375
1440
1480
2900
2920
2970

| Mass Spectral Analysis is as follows: | |
| --- | --- |
| m/e | Relative Intensity |
| 43 | 100[1] |
| 46 | 24 |
| 51 | 18 |
| 54 | 33 |
| 55 | 39 |
| 60 | 60[4] |
| 77 | 42[6] |
| 88 | 67[3] |
| 105 | 50[5] |
| 121 | 89[2] |
| M208 | 15 |

This material has a fruity, sulfury, vegetable aroma with yeasty and vitamin B complex-like nuances, and a fruity, sulfury, albedo-like flavor with yeasty and citrus-like nuances.

EXAMPLE X

Preparation of Ethyl-2,6-Dimethyl-1,3-Oxathiane-2-Acetate

Reaction:

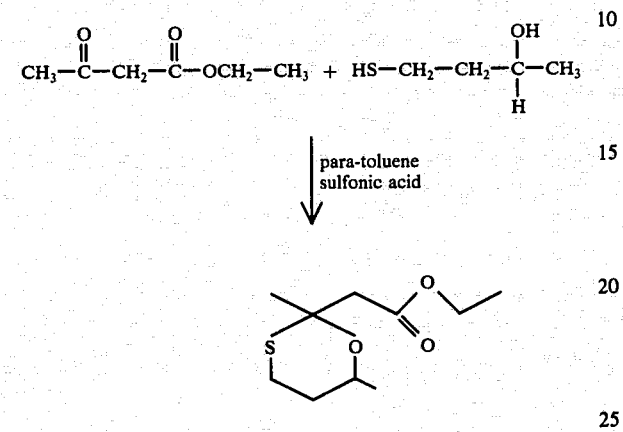

para-toluene sulfonic acid

Procedure:

75 ml of dichloromethane is placed into a 100 ml round-bottom flask. To the dichloromethane is added 5.3 grams (0.05 moles) of 4-mercapto-2-butanol. 7.14 grams (0.055 moles) ethyl acetoacetate is then added followed by 0.1 grams of p-toluene sulfonic acid. Boiling chips are added to the flask. A Dean-Starke distilling receiver is placed on the flask, and a reflux condenser is placed on the receiver. The flask is then heated slowly until reflux occurs, and then the temperature is increased for a more vigorous reflux. The reflux lasts for a period of 2 hours before water of reaction ceases to be formed. The reaction mass is then cooled and neutralized with 10% aqueous sodium bicarbonate to a pH of 8. The reaction mass is filtered through fluted filter paper, and the dichloromethane solvent by means of rotary evaporation. 9.8 grams of crude product are recovered after the rotary evaporation operation. The crude product is then distilled by means of vacuum distillation yielding the following 4 fractions:

| Fraction No. | Vapor Temp. | Pressure (mm Hg) | Weight of Fraction |
|---|---|---|---|
| 1 | 27° | 0.025 | 0.9 g |
| 2 | 69 | 0.075 | 0.5 |
| 3 | 69 | 0.075 | 2.2 |
| 4 | 66 | 0.075 | 1.5 |

NMR, IR and Mass Spectral analyses yield the information that the resulting reaction product is:

| m/e | Relative Intensity |
|---|---|
| 55 | 39 |
| 60 | 60[4] |
| 77 | 42[6] |
| 88 | 67[3] |
| 105 | 50[5] |
| 121 | 89[2] |
| M208 | 15 |

Mass Spectral Analysis is as follows:

| m/e | Relative Intensity |
|---|---|
| 27 | 20 |
| 29 | 30 |
| 43 | 100[1] |
| 46 | 27 |
| 54 | 36 |
| 55 | 58[4] |
| 60 | 64[3] |
| 85 | 53[6] |
| 88 | 70[2] |
| 131 | 54[5] |
| M218 | 5 |

NMR Analysis is as follows:

| | | |
|---|---|---|
| 1.12 ppm (d) | $CH_3-\overset{H}{\underset{}{C}}-O-$ | 3H |
| 1.25 (t) | $CH_3-C-O-\overset{O}{\underset{\|}{C}}$ | 3H |
| 1.64 (s) <br> 1.80 (s) | $\overset{CH_3}{\underset{S\quad O}{\diagdown\diagup}}$ | 3H |
| 1.74–1.5 (m) | $\diagdown_{CH_2}$ | 2H |
| 2.60 (m) <br> 2.74 (m) | HC—S— | |
| | $-S-\overset{\|}{\underset{-O}{C}}-CH_2-\overset{O}{\underset{\|}{C}}-O$ | 4H |
| 3.44–2.98 (m) | HC—S— | |
| 3.97 (m) | Me—C—O— <br> H | 1H |
| 4.13 (q) | Me—CH$_2$—O—$\overset{O}{\underset{\|}{C}}$— | 2H |

IR Analysis is as follows:
825 cm$^{-1}$
980
1025
1050
1080
1125
1175
1200
1280
1305
1360
1440
1725
2900

2930
2970

This material has a sweet, sulfury, meaty aroma and taste.

EXAMPLE XI

Preparation of 2-Nonyl-6-Methyl-1,3-Oxathiane

Reaction:

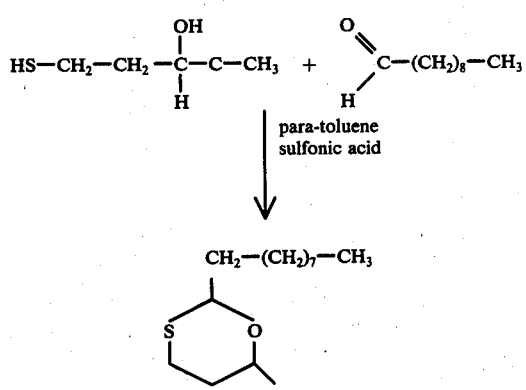

Procedure:

75 ml of dichloromethane is placed in a 100 ml round-bottom flask. To the dichloromethane is added 5.3 grams (0.05 moles) of 4-mercapto-2-butanol. 8.58 grams (0.055 moles) n-decanal is then added followed by 0.1 grams of p-toluene sulfonic acid. Boiling chips are added to the flask. A Dean-Starke distilling receiver is placed on the flask, and a reflux condenser is placed on the receiver. The flask is then heated slowly until reflux occurs, and then the temperature is increased for a more vigorous reflux. The reflux lasts for a period of 2 hours before water of reaction ceases to be formed. The reaction mass is then cooled and neutralized with 10% aqueous sodium bicarbonate to a pH of 8. The reaction mass is filtered through fluted filter paper, and the dichloromethane solvent is removed by means of rotary evaporation. 11.8 grams of crude product are recovered after the rotary evaporation operation. The crude product is then distilled by means of vacuum distillation yielding the following 4 fractions:

| Fraction No. | Vapor Temp. | Pressure (mm Hg) | Weight of Fraction |
|---|---|---|---|
| 1 | 65-104° C. | 0.9 | 0.8 |
| 2 | 98 | 0.1 | 1.7 |
| 3 | 95 | 0.025 | 4.3 |
| 4 | 85 | — | 0.7 |

NMR, IR and Mass Spectral analyses yield the information that the resulting reaction product is:

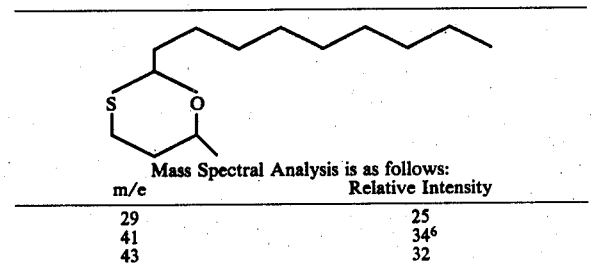

Mass Spectral Analysis is as follows:

| m/e | Relative Intensity |
|---|---|
| 29 | 25 |
| 41 | 34[6] |
| 43 | 32 |
| 46 | 23 |
| 47 | 20 |
| 54 | 37[5] |

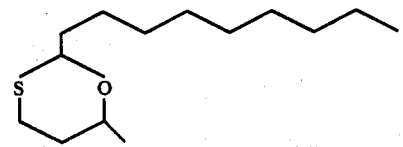

Mass Spectral Analysis is as follows:

| m/e | Relative Intensity |
|---|---|
| 55 | 78[2] |
| 60 | 55[3] |
| 88 | 48[4] |
| 117 | 100[1] |
| M244 | 3 |

NMR Analysis is as follows:

| 0.86 ppm (t) | $CH_3-CH_2-$ | 3H |
|---|---|---|
| 1.18 (d) | $CH_3-\overset{H}{\underset{}{C}}-O-$ | |
| 1.25 (broad) | $-CH_2-$ | 21H |
| 1.85-1.44 (m) | $-CH_2-$ | |
| 2.78 and 2.64 (m) | $HC-S-$ | 1H |
| 2.52 (m) | $HC-S-$ | 1H |
| 3.49 (m) | $Me-\overset{H}{\underset{}{C}}-O-$ | 1H |
| 4.77 (t) | $CH_2-\overset{O-}{\underset{H}{C}}-S-$ | 1H |

IR Analysis is as follows:
1000 cm$^{-1}$
1050
1080
1200
1275
1360
1380
1415
1425
1435
1455
2840
2920
2950

This material has a sweet, sulfury roasted vegetable-like aroma and taste, at levels of from 0.01 up to 0.1 ppm. At 0.2 ppm spearmint-like notes are present.

EXAMPLE XII

Preparation of 7-Methyl(6-Oxa-10-Thiaspiro)4.5-Decane

Reaction:

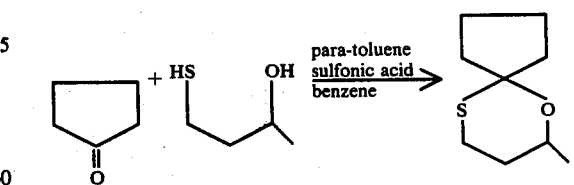

Procedure:

Into a 100 ml round-bottom flask equipped with a Dean-Starke trap and condenser, the following materials are added:

| 4-mercapto-2-butanol | 5.3 g (0.05 moles) |
|---|---|
| cyclopentanone | 4.6 g (0.055 moles) |

| | | |
|---|---|---|
| benzene | 100 ml | |
| para-toluene sulfonic acid | 0.1 g | |

The resulting reaction mass is refluxed for a period of 2 hours, after which time the reaction mass is cooled and extracted with 15 ml of a 10% aqueous sodium bicarbonate solution. The reaction mass is then extracted using two 15 ml portions of distilled water. The resulting material is dried over anhydrous sodium sulfate, and the benzene solvent is removed by means of rotary evaporation. The resulting product is then fractional distilled yielding the following 4 fractions:

| Fraction No. | Vapor Temp. | Pressure (mm Hg) | Weight of Fraction | Purity |
|---|---|---|---|---|
| 1 | 35–70° C | 2.2 | 0.6 g | 96.08% |
| 2 | 72 | 2.6 | 2.2 | 99.57% |
| 3 | 70 | 2.7 | 1.9 | 99.28% |
| 4 | 45 | 2.5 | 0.6 | 96.0% |

NMR, IR and Mass Spectral analyses yield the information that the resulting reaction product has the structure:

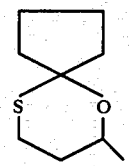

Mass Spectral Analysis is as follows:

| m/e | Relative Intensity |
|---|---|
| 27 | 53[5] |
| 39 | 35 |
| 41 | 45[6] |
| 45 | 28 |
| 46 | 35 |
| 54 | 35 |
| 55 | 100[1] |
| 60 | 65[3] |
| 85 | 55[4] |
| 88 | 75[2] |
| M172 | 9 |

The NMR Analysis is as follows:

| 1.12 ppm (d) | $CH_3-\overset{H}{\underset{}{C}}-O-$ | 3H |
|---|---|---|
| 2.28–1.40 (m) | $-CH_2-$ | 10H |
| 2.68 and 2.54 (m) | $HC-S-$ | 1H |
| 3.05 (m) | $HC-S-$ | 1H |
| 3.77 (m) | $Me-\overset{H}{\underset{}{C}}-O-$ | 1H |

The IR Analysis is as follows:
925 cm$^{-1}$
955
1005
1055
1080
1180
1200
1320
1365
1375
1440
2870
2900
2940
2960

This material has a sweet, beefy, fruity aroma with a berry-like nuance and a sweet, fruity, floral flavor with berry, "mouthfeel" and green nuances.

EXAMPLE XIII

At the rate of 3 ppm (based on liquid; 30 ppm based on solid) to an orange drink prepared using "Tang" (manufactured by the General Foods Corporation of White Plains, New York) (100 gms solid/liter water) is added 2,6-dimethyl-2-phenyl-1,3-oxathiane, prepared according to the process of Example IX. A second "Tang" drink is prepared in the same manner without the oxathiane derivative. The "Tang" drink containing the 2,6-dimethyl-2-phenyl-1,3-oxathine is preferred by a bench panel as having an improved orange juice-like aroma and a taste reminiscent of fresh orange juice.

EXAMPLE XIV

Orange juice (manufactured by Sharp and Sharp Inc. of Boston, Massachusetts) is prepared (100 gm concentrate/liter of water). To one portion of said orange juice is added 2,6-dimethyl-2-phenyl-1,3-oxathiane prepared according to the process of Example IX (at the rate of 1 ppm based on liquid beverage). A second portion of the orange juice had no flavor additive added thereto. The aroma and taste characteristics which are present in fresh orange juice are added using the 2,6-dimethyl-2-phenyl-1,3-oxathiane. The resulting product with the oxathiane derivative is considered by a bench panel to be substantially improved as compared to the material without the oxathiane derivative added thereto.

The use level range of the 2,6-dimethyl-2-phenyl-1,3-oxathiane is from 0.1 ppm up to 10 ppm based on total weight of finished product.

EXAMPLE XV

The following basic strawberry formulation is prepared:

| Ingredient | Parts by Weight |
|---|---|
| para-hydroxy benzyl acetone | 5 |
| vanillin | 15 |
| maltol | 20 |
| ethyl methyl phenyl glycidate | 15 |
| ethyl butyrate | 20 |
| ethyl benzoate | 1 |
| methyl cinnamate | 5 |
| methyl anthranilate | 1 |
| gamma undecalactone | 2 |
| diacetyl | 2 |
| cis-3-hexenol | 20 |
| anethole | 1 |
| ethyl acetate | 13 |
| ethanol (95% aqueous) | 180 |
| propylene glycol | 700 |

7-methyl(6-oxa-10-thiaspiro)4.5-decane prepared according to the process of Example XII is added to a portion of the above formulation at the rate of 1%. Two formulations; one with and one without the 7-methyl(6-oxa-10-thiaspiro)4.5-decane, are each added at the rate of 50 ppm to water and tested by a bench panel. The panel unanimously prefers as having fresh, green, strawberry topnotes and the taste of fresh-picked strawberries, the flavor formulation which contains the 7-methyl(6-oxa-10-thiaspiro)4.5-decane.

EXAMPLE XVI

The following basic raspberry formulation is prepared:

| Ingredient | Parts by Weight |
| --- | --- |
| para-hydroxy benzyl acetone | 4 |
| vanillin | 1 |
| maltol | 2 |
| α-ionone (10% in 95% aqueous ethanol) | 2 |
| isobutyl acetate | 20 |
| ethyl butyrate | 5 |
| dimethyl sulfide | 1 |
| acetic acid | 10 |
| acetaldehyde | 15 |
| propylene glycol | 940 |

To 50% of the above formulation, 7-methyl(6-oxa-10-thiaspiro)4.5-decane, prepared according to the process of Example XII is added at the rate of 0.5%. No such material (or any other additive) is added to the other 50% of this formulation. The two formulations are compared at 0.005% (50 ppm), in water, by a bench panel. The flavor containing the 7-methyl(6-oxa-10-thiaspiro)4.5-decane, prepared according to the process of Example XII, has more natural notes of the ripe berry and an additional note reminiscent of raspberry seeds. It is unanimously preferred by a bench panel over the formulation not containing the 7-methyl(6-oxa-10-thiaspiro)4.5-decane.

EXAMPLE XVII 2-methyl-1,3-oxathiolane, prepared according to the process of Example I, is added to a 1% solution of Wyler's "Beef Flavored Instant Bouillon" (manufactured by Wyler Foods, Division of Borden, Inc., Chicago, Illinois, U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 0.2 ppm. The resulting beef flavor has sweet, meaty notes, a desired bloody character and a meat extract character added to the rather otherwise flat, salty beef broth. The sweet, bloody notes of the 2-methyl-1,3-oxathiolane increase the mouthfeel of broth, which is also desirable. The use level of 2-methyl-1,3-oxathiolane is in the range of from 0.05 ppm up to 5 ppm.

EXAMPLE XVIII 2-isobutyl-1,3-oxathiolane, prepared according to the process of Example VIII, is added to a 1% solution of Wyler's "Beef Flavored Instant Bouillon" (manufactured by Wyler Foods, Division of Borden, Inc., Chicago, Illinois, U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 0.1 ppm. The salty character of the beef broth is depressed by use of the 2-isobutyl-1,3-oxathiolane, and a vegetable note and an especially pleasant light burning aftertaste are added. In addition, the beef broth character is improved by the use of the 2-isobutyl-1,3-oxathiolane.

EXAMPLE XIX

Hellmann's Mayonaise (manufactured by the Best Foods Division of CPC, Inc., of Englewood Cliffs, New Jersey) has added thereto at the rate of 3ppm, 2-isobutyl-1,3-oxathiolane, prepared according to the process of Example VIII. The 2-isobutyl-1,3-oxathiolane added at the level of 3 ppm adds a sensation described as "horseradish-like having a burning sensation" in the mouth; and this is considered to be a great improvement over the Mayonaise without the 2-isobutyl-1,3-oxathiolane. The use level of the 2-isobutyl-1,3-oxathiolane is from 0.5 ppm up to 20 ppm, depending on the intensity of the horseradish-like note and burning sensation desired.

EXAMPLE XX 2,2-dimethyl-1,3-oxathiolane, prepared according to the process of Example VII, is added to a 1% solution of Wyler's "Beef Flavored Instant Bouillon" (manufactured by Wyler Foods, Division of Borden, Inc., Chicago, Illinois, U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 2 ppm. The 2,2-dimethyl-1,3-oxathiolane added at this rate increases the vegetable character of the beef broth, especially the celery character; and depresses the salt character. The mouthfeel and overall quality of the beef broth are also important. The beef broth is unanimously considered by a bench panel to be greatly improved when the 2,2-dimethyl-1,3-oxathiolane is added at the level of 2 ppm. The use level of the 2,2-dimethyl-1,3-oxathiolane is from 0.2 up to 5 ppm.

EXAMPLE XXI

The following basic raspberry formulation is prepared:

| Ingredient | Parts by Weight |
| --- | --- |
| para-hydroxy benzyl acetone | 4 |
| vanillin | 1 |
| maltol | 2 |
| α-ionone (10% in propylene glycol) | 2 |
| isobutyl acetate | 20 |
| ethyl butyrate | 5 |
| dimethyl sulfide | 1 |
| acetic acid | 10 |
| acetaldehyde | 15 |
| propylene glycol | 940 |

Adding to this basic raspberry formulation 1% by weight of 2,6-dimethyl-1,3-oxathiane, (prepared according to the process of Example II) adds a ripe fruit character to this raspberry flavored formulation. The comparisons are carried out at the rate of 100 ppm in water. The use level of the 2,6-dimethyl-1,3-oxathiane is from 0.05 ppm up to 10 ppm.

EXAMPLE XXII

At the rate of 0.2 ppm, 2,6-dimethyl-1,3-oxathiane, prepared according to the process of Example II, is added to imitation maple syrup (Vermont Maid Syrup, manufactured by R.J.R. Foods Inc., of Winston Salem, North Carolina). The 2,6-dimethyl-1,3-oxathiane, prepared according to Example II, increases the maple character and makes it more natural by adding more aroma and improving the taste substantially. The maple syrup having the 2,6-dimethyl-1,3-oxathiane added thereto is unanimously preferred by a bench panel.

EXAMPLE XXIII 2-isobutyl-6-methyl-1,3-oxathiane, prepared according to the process of Example VI, is added to a 2% solution of Wyler's "Beef Flavored Instant Bouillon" (manufactured by Wyler Foods, Division of Borden, Inc., Chicago, Illinois, U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 0.1 ppm. The resulting material has added thereto a spicy, vegetable aroma; and the 2-isobutyl-6-methyl-1,3-oxathiane causes the beef broth aroma to be rounded out because more mouthfeel is added thereto as a result of the use of the 2-isobutyl-6-methyl-1,3-oxathiane.

EXAMPLE XXIV

To Ann Page Condensed Vegetable Soup (produced by The Great Atlantic and Pacific Tea Company, Inc.) at the rate of 0.3 ppm is added 2-isobutyl-6-methyl-1,3-oxathiane, prepared according to the process of Example VI. The 2-isobutyl-6-methyl-1,3-oxathiane adds spicy, and vegetable aromas and increases the mouthfeel of the resulting vegetable soup. The level of the 2-isobutyl-6-methyl-1,3-oxathiane can be increased up to 0.7 ppm with higher levels of oxathiane thereby creating increased spiciness. The use level of the 2-isobutyl-6-methyl-1,3-oxathiane is in the range of from 0.02 ppm up to 5 ppm.

EXAMPLE XXV

At the rate of 0.5 ppm, 2,6-trimethyl-1,3-oxathiane, prepared according to the process of Example V, is added to Ann Page Vegetarian Vegetable Soup (produced by the Great Atlantic and Pacific Tea Company, Inc). At this level the 2,2,6-trimethyl-1,3-oxathiane adds a black-pepper aroma and taste with a burning sensation. A bench panel unanimously prefers the vegetarian vegetable soup with the 2,2,6-trimethyl-1,3-oxathiane added thereto.

EXAMPLE XXVI 2,2,6-trimethyl-1,3-oxathiane, prepared according to the process of Example V, is added to a 1.5% solution of Wyler's "Beef Flavored Instant Bouillon" (manufactured by Wyler Foods, Division of Borden, Inc. Chicago, Illinois, U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 0.2 ppm. The 2,2,6-trimethyl-1,3-oxathiane added at this rate adds a pleasant, black-pepper aroma and taste to the Wyler's bouillon, and the resulting bouillon is preferred unanimously by a bench panel over that bouillon not flavored by the 2,2,6-trimethyl-1,3-oxathiane. The use level range of the 2,2,6-trimethyl-1,3-oxathiane is from 0.05 up to 10 ppm.

EXAMPLE XXVII

A. POWDER FLAVOR

20 Grams of any of the flavor compositions of Examples XV, XVI or XXI each of which flavor compositions contains a flavor imparting or enhancing amount of substituted oxathiane compound, is emulsified in a solution containing 300 gm gum acacia and 700 gm water. The emulsion is spray-dried with a Bowen Lab Model Drier utilizing 250 c.f.m. of air with an inlet temperature of 500° F., and outlet temperature of 200° F., and a wheel speed of 50,000 r.p.m.

B. PASTE BLEND

| Ingredient | Parts by Weight |
|---|---|
| Liquid Flavor Composition of any of Examples XV, XVI or XXI each of which flavor compositions contains a flavor imparting or flavor enhancing amount of substituted oxathiane compound. | 48.4 |
| Cab-O-Sil ®M-5 (Brand of Silica produced by the Cabot Corporation of 125 High Street, Boston, Mass. 02110; Physical Properties: Surface Area: 200 m²/gm Nominal Particle Size: 0.012 microns Density: 2/3 lbs/cu.ft. | 3.2 |

The Cab-O-Sil is dispersed in any of the exemplified liquid flavor compositions with vigorous stirring, thereby resulting in a viscous liquid. 48.4 Parts by weight of the powder flavor composition prepared in Part A is then blended into the said viscous liquid, with stirring at 25° C for a period of 30 minutes, resulting in a thixotropic sustained release flavor paste.

EXAMPLE XXVIII

Chewing Gum

100 Parts by weight of chicle are mixed with 4 parts by weight of the flavor prepared in accordance with Example XXVII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing the chewing gum has a pleasant long lasting fruity flavor (e.g. raspberry or strawberry).

EXAMPLE XXIX

Toothpaste Formulation

The following separate groups of ingredients are prepared:

| Group "A" | |
|---|---|
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium n-Lauroyl Sarcosinate (foaming agent) |
| Group "D" | |
| 1.200 | Flavor Material of Example XXVII |
| 100.00 (Total) | |

PROCEDURE
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.

| | |
|---|---|
| 5. | The resultant slurry is then blended for one hour. The completed paste is then transferred to a three roller mill and then homogenized, and finally tubed. |

The resulting toothpaste when used in a normal toothbrushing procedure yields a pleasant fruity flavor (e.g. raspberry or strawberry) of constant strong intensity throughout said procedure (1–1.5 minutes).

EXAMPLE XXX

Chewable Vitamin Tablets

The favor material produced according to the process of Example XXVII is added to the Chewable Vitamin Tablet Formulation at the rate indicated, which Chewable Vitamin Tablet Formulation is prepared as follows:

| | Gms/1000 tablets |
|---|---|
| Vitamin C (ascorbic acid) as ascorbic acid-sodium ascorbate mixture 1:1 | 70.0 |
| Vitamin B$_1$ (thiamine mononitrate) as Rocoat$^R$ thiamine mononitrate 33 ⅓% (Hoffman La Roche) | 4.0 |
| Vitamin B$_2$ (riboflavin) as Rocoat $^R$ riboflavin 33 ⅓% | 5.0 |
| Vitamin B$_6$ (pyridoxine hydrochloride) as Rocoat$^R$ pyridoxide hydrochloride 33 ⅓% | 4.0 |
| Niacinamide as Rocoat$^R$ niacinamide 33 ⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33 ⅓% Roche | 6.6 |
| d-Biotin | 0.044 |
| Certified lake color | 5.0 |
| Flavor of Example XXVII | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablet yeilds a pleasant, longlasting, consistently strong fruit flavor (e.g. raspberry or strawberry) for a period of 12 minutes.

EXAMPLE XXXI

6-Methyl-2-phenyl-1,3-oxathiane, prepared according to the process of Example III is added to a 2% soluton of Wyler's "Beef Flavored Instant Bouillon" (manufactured by Wyler Foods, Division of Borden, Inc., Chicago, Illinois, U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 3.0 ppm. The resulting material has added thereto a more roasted aroma and pot roast-like notes; and causes the beef broth aroma to have cooked beef notes and have the hydrolyzed vegetable protein notes more depressed, and have a more rounded flavor.

EXAMPLE XXXII

Ethyl-2,6-dimethyl-1,3-oxathiane-2-acetate prepared according to the process of Example X is added to a 1.5% solution of Wyler's "Beef Flavored Instant Bouillon" (manufactured by Wyler Foods, Division of Borden, Inc., Chicago, Illinois, U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 20 ppm. The ethyl-2,6-dimethyl-1,3-oxathiane-2-acetate added at this rate adds pleasant, sweet, meaty notes to the Wyler's bouillon, and the resulting bouillon's hydrolyzed vegetable protein character is rounded out.

EXAMPLE XXXIII

2-Nonyl-6-methyl-1,3-oxathiane, prepared according to the process of Example XI, is added to a 1.5% solution of Wyler's "Beef Flavored Instant Bouillon" (manufactured by Wyler Foods, Division of Borden, Inc., Chicago, Illinois, U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 0.1 ppm. The resulting beef flavor has more roasted notes, improves the mouthfeel and depresses the hydrolyzed vegetable protein-like character of the rather otherwise, flat, salty beef broth.

EXAMPLE XXXIV

2-Nonyl-6-methyl-1,3-oxathiane prepared according to Example XI added at the rate of 0.5% to a synthetic spearmint oil (sold by SCM Corp. (Glidden-Durkee Div.)) is compared with the same spearmint oil without the 6-methyl-2-nonyl-1,3-oxathiane. Both are compared in water at the rate of 20 ppm by a bench panel. The oil containing 6-methyl-2-nonyl-1,3-oxathiane is considered as having more of the sweet characteristic spearmint notes as the present in natural spearmint oil and is therefore preferred.

What is claimed is:

1. An oxathio heterocyclic compound which is 2-n-nonyl-6-methyl-1,3-oxathiane having the structure:

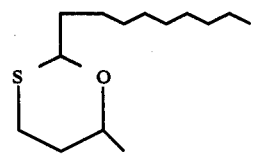

2. An oxathio heterocyclic compound which is 2,6-dimethyl-2-acetyl-1,3-oxathiane having the structure:

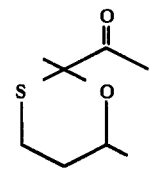

* * * * *